(12) United States Patent
Huang

(10) Patent No.: US 8,796,901 B2
(45) Date of Patent: Aug. 5, 2014

(54) MICRO-ELECTRO-MECHANICAL TRANSDUCER HAVING AN INSULATION EXTENSION

(75) Inventor: Yongli Huang, San Jose, CA (US)

(73) Assignee: Kolo Technologies, Inc., San Jose, CA (US)

( * ) Notice: Subject to any disclaimer, the term of this patent is extended or adjusted under 35 U.S.C. 154(b) by 266 days.

(21) Appl. No.: 11/917,666

(22) PCT Filed: Jun. 16, 2006

(86) PCT No.: PCT/IB2006/051948
§ 371 (c)(1),
(2), (4) Date: Dec. 14, 2007

(87) PCT Pub. No.: WO2006/134580
PCT Pub. Date: Dec. 21, 2006

(65) Prior Publication Data
US 2008/0290756 A1      Nov. 27, 2008

Related U.S. Application Data

(60) Provisional application No. 60/692,038, filed on Jun. 17, 2005, provisional application No. 60/705,606, filed on Aug. 3, 2005, provisional application No. 60/744,242, filed on Apr. 4, 2006.

(51) Int. Cl.
*H02N 1/00* (2006.01)
*H04R 19/00* (2006.01)
*B81B 3/00* (2006.01)

(52) U.S. Cl.
USPC ............................. 310/309; 438/53; 367/181

(58) Field of Classification Search
USPC ..................... 438/50–53, 117; 310/309, 300; 600/459; 381/174, 191, 181; 367/163, 367/181; 73/514.32
See application file for complete search history.

(56) References Cited

U.S. PATENT DOCUMENTS

| | | | |
|---|---|---|---|
| 2,975,307 A | 3/1961 | Schroeder et al. | |
| 4,889,832 A | 12/1989 | Chatterjee | |
| 4,996,627 A | 2/1991 | Zias et al. | |

(Continued)

FOREIGN PATENT DOCUMENTS

| | | |
|---|---|---|
| EP | 1306901 A2 | 5/2003 |
| JP | 05047916 | 2/1993 |

(Continued)

OTHER PUBLICATIONS

Higuchi, JP2002-250665A Machine Translation, Sep. 2002.*

(Continued)

*Primary Examiner* — Burton Mullins
*Assistant Examiner* — Eric Johnson
(74) *Attorney, Agent, or Firm* — Lee & Hayes, PLLC

(57) ABSTRACT

A micro-electro-mechanical transducer (such as a cMUT) having two electrodes separated by an insulator with an insulation extension is disclosed. The two electrodes define a transducing gap therebetween. The insulator has an insulating support disposed generally between the two electrodes and an insulation extension extending into at least one of two electrodes to increase the effective insulation without having to increase the transducing gap. Methods for fabricating the micro-electro-mechanical transducer are also disclosed. The methods may be used in both conventional membrane-based cMUTs and cMUTs having embedded springs transporting a rigid top plate.

45 Claims, 23 Drawing Sheets

(56) References Cited

U.S. PATENT DOCUMENTS

| | | | |
|---|---|---|---|
| 5,055,731 | A | 10/1991 | Nihei et al. |
| 5,146,435 | A | 9/1992 | Bernstein |
| 5,510,276 | A * | 4/1996 | Diem et al. ............... 438/53 |
| 5,894,452 | A | 4/1999 | Ladabaum et al. |
| 5,993,677 | A | 11/1999 | Biasse et al. |
| 6,002,117 | A | 12/1999 | Pak |
| 6,004,832 | A | 12/1999 | Haller et al. |
| 6,283,601 | B1 | 9/2001 | Hagelin et al. |
| 6,314,057 | B1 | 11/2001 | Solomon et al. |
| 6,512,625 | B2 | 1/2003 | Mei et al. |
| 6,558,330 | B1 | 5/2003 | Ayter et al. |
| 6,585,653 | B2 * | 7/2003 | Miller ..................... 600/459 |
| 6,600,587 | B2 | 7/2003 | Sniegowski et al. |
| 6,605,518 | B1 | 8/2003 | Ohmi et al. |
| 6,684,469 | B2 | 2/2004 | Horning et al. |
| 6,828,656 | B2 | 12/2004 | Forbes et al. |
| 6,865,140 | B2 | 3/2005 | Thomenius et al. |
| 7,030,536 | B2 | 4/2006 | Smith et al. |
| 7,052,464 | B2 * | 5/2006 | Wodnicki ............... 600/459 |
| 7,489,593 | B2 | 2/2009 | Nguyen-Dinh et al. |
| 7,564,172 | B1 | 7/2009 | Huang |
| 8,345,513 | B2 | 1/2013 | Huang |
| 2002/0031294 | A1 | 3/2002 | Takeda et al. |
| 2002/0074670 | A1 | 6/2002 | Suga |
| 2003/0022475 | A1 | 1/2003 | Vieux-Rochaz et al. |
| 2003/0207566 | A1 | 11/2003 | Forbes et al. |
| 2003/0222354 | A1 | 12/2003 | Mastromatteo et al. |
| 2004/0027671 | A1 | 2/2004 | Wu et al. |
| 2004/0085858 | A1 * | 5/2004 | Khuri-Yakub et al. ....... 367/181 |
| 2004/0106221 | A1 | 6/2004 | Hunter et al. |
| 2005/0046922 | A1 | 3/2005 | Lin et al. |
| 2005/0075572 | A1 | 4/2005 | Mills et al. |
| 2005/0168849 | A1 * | 8/2005 | Lin ..................... 359/850 |
| 2005/0237858 | A1 | 10/2005 | Thomenius et al. |
| 2006/0004289 | A1 * | 1/2006 | Tian et al. ............... 600/459 |
| 2006/0075818 | A1 | 4/2006 | Huang et al. |
| 2006/0125348 | A1 | 6/2006 | Smith et al. |
| 2008/0194053 | A1 | 8/2008 | Huang |
| 2008/0197751 | A1 | 8/2008 | Huang |
| 2008/0203556 | A1 | 8/2008 | Huang |
| 2008/0290756 | A1 * | 11/2008 | Huang ..................... 310/300 |
| 2009/0140606 | A1 | 6/2009 | Huang |

FOREIGN PATENT DOCUMENTS

| | | |
|---|---|---|
| JP | 2000508860 | 7/2000 |
| JP | 2002076269 | 3/2002 |
| JP | 2002191180 | 7/2002 |
| JP | 2002250665 | 9/2002 |
| JP | 2003017503 | 1/2003 |
| JP | 2003078080 | 3/2003 |
| JP | 2003151978 | 5/2003 |
| JP | 2003526207 | 9/2003 |
| JP | 2004333502 | 11/2004 |
| JP | 2005078068 | 3/2005 |
| JP | 2008541434 | 11/2008 |
| WO | WO2004084300 A1 | 9/2004 |
| WO | WO2005120130 A1 | 12/2005 |

OTHER PUBLICATIONS

Chow et al, "Process Compatible Polysilicon-Based Electrical Through-Wafer Interconnects in Silicon Substrates," Journal of Electromechanical Systems, IEEE, vol. 11, No. 6, Dec. 2002, pp. 631-640.

Ergun et al, "Capacitive Micromachined Ultrasonic Transducers: Fabrication Technology," IEEE Transactions on Ultrasonics, Ferroelectrics, and Frequency Control, vol. 52, No. 12, Dec. 2005, pp. 2242-2258.

Huang et al, "Fabricating Capacitive Micromachined Ultrasonic Transducers with Wafer-Bonding Technology," Journal of Microelectromechanical Systems, IEEE, vol. 12, No. 2, Apr. 2003, pp. 128-137.

Jin et al, "Micromachined Capacitive Transducer Arrays for Medical Ultrasound Imaging," 1998 IEEE Ultrasonics Symposium, pp. 1877-1880.

Lemmerhirt et al, "Air-Isolated Through-Wafer Interconnects for Microsystem Applications," The 12th International Conference on Solid State Sensors, Actuators and Microsystems, IEEE, Jun. 6-12, 2003, pp. 1067-1070.

Jin et al, "Recent Progress in Capacitive Micromachined Ultrasonic Immersion Transducer Array," The 8th International Symposium on Integrated Circuits, Devices and Systems, Singapore, Sep. 8-10, 1999, pp. 159-162.

Douglass et al, "Why is the Texas Instruments Digital Micromirror Device(TM) (DMD(TM)) so Reliable?", 1997, 7 pgs.

Hornbeck et al, "Digital Light Processing and MEMS: Timely Convergence for a Bright Future," DLP—Digital Light Processing, 1995, 25 pgs.

Huang et al, "Capacitive Micromachined Ultrasonic Transducers (CMUTS) with Isolation Posts," 2004 IEEE International Ultrasonics, Ferroelectrics, and Frequency Control Joint 50th Anniversary Conference, pp. 2223-2226.

Huang et al, "New Fabrication Process for Capacitive Micromachined Ultrasonic Transducers," IEEE, 2003, pp. 522-525.

Huang et al, "Optimized Membrane Configuration Improves CMUT Performance," 2004 IEEE Ultrasonics Symposium, 2004 IEEE International Ultrasonics, Ferroelectrics, and Frequency Control Joint 50th Anniversary Conference, pp. 505-508.

Hwang et al, "Design and Fabrication of the Thin-Film Micromirror Array-actuated for Large Projection Displays," Journal of the Korean Physical Society, vol. 33, Nov. 1998, pp. S467-S470.

Jeon et al, "Electrostatic Digital Micromirror Using Interdigitated Cantilevers," IEEE, 2002, pp. 528-531.

Khuri-Yakub et al, "Micromachined Ultrasonic Transducers and Their Use for 2D and 3D Imaging," Acoustical Imaging, Kluwer Academic Publishers, Netherlands, 2004, pp. 1-9.

Kim et al, "A High Fill-Factor Micro-Mirror Stacked on a Crossbar Torsion Spring for Electrostatically-Actuated Two-Axis Operation in Large-Scale Optical Switch," IEEE, 2003, pp. 259-262.

Zhou et al, "Two-Axis Scanning Mirror for Free-Space Optical Communication between UAVs," IEEE/LEOS Optical MEMS 2003, Hawaii, US, Aug. 2003, pp. 1-2.

Huang et al, "Capacitive Micromachined Ultrasonic Transducers (CMUTS) with Piston-Shaped Membranes," 2005 IEEE Ultrasonics Symposium, 2005, pp. 589-592.

PCT International Search Report and Written Opinion for PCT Application No. PCT/IB06/51567, mailed on Jun. 5, 2008, 7 pgs.

PCT International Search Report and Written Opinion for PCT Application No. PCT/IB06/51568, mailed on Jun. 16, 2008, 7 pgs.

PCT International Search Report and Written Opinion for PCT Application No. PCT/IB06/51569, mailed on Jun. 18, 2008, 7 pgs.

PCT International Search Report and Written Opinion for PCT Application No. PCT/IB06/51948, mailed on Jul. 7, 2008, 9 pgs.

Extended Europoean Search Report mailed on Feb. 18, 2011 for European Patent Application No. 06744966.0, a counterpart foreign application for U.S. Appl. No. 11/914,584.

Translated Japanese Office Action mailed Oct. 21, 2011 for Japanese patent application No. 2008-516496, a counterpart foreign application of U.S. Appl. No. 11/917,666, 6 pages.

Non-Final Office Action for U.S. Appl. No. 11/914,597, mailed on Nov. 4, 2011, Yongli Huang, "Micro-Electro-Mechanical Transducers", 21 pages.

Translated Chinese Office Action mailed Nov. 14, 2011 for Chinese patent application No. 200680025783.2, a counterpart foreign application of U.S. Appl. No. 11/914,584, 11 pages.

Translated Chinese Office Action mailed Dec. 16, 2011 for Chinese patent application No. 200680021083.6, a counterpart foreign application of U.S. Appl. No. 11/917,666, 5 pages.

Translated Chinese Office Action mailed Mar. 23, 2011 for Chinese Patent Application No. 200680017137.1, a counterpart foreign application of U.S. Appl. No. 11/914,597.

Non-Final Office Action for U.S. Appl. No. 11/914,584 mailed on Apr. 25, 2011, Yongli Huang, "Through-Wafer Interconnection".

(56) References Cited

OTHER PUBLICATIONS

Japanese Office Action and English Translation mailed Jul. 8, 2011 for Japanese patent application No. 2008-511848, a counterpart foreign application of U.S. Appl. No. 11/914,597.

Office action for U.S. Appl. No. 11/914,608, mailed on Aug. 4, 2011, Huang, "Micro-Electro-Mechanical Transducers", 8 pages.

Translated Chinese Office Action mailed Aug. 3, 2012 for Chinese patent application No. 200680021083.6, a counterpart foreign application of U.S. Appl. No. 11/917,666, 6 pages.

Translated Japanese Office Action mailed Apr. 27, 2012 for Japanese patent application No. 2008-516496, a counterpart foreign application of U.S. Appl. No. 11/917,666, 4 pages.

Translated Japanese Office Action mailed May 18, 2012 for Japanese patent application No. 2008-511846, a counterpart foreign application of US patent No. 8,105,941, 8 pages.

Extended European Search Report mailed Apr. 10, 2012 for European patent application No. 06756136.5, 7 pages.

Chinese Office Action mailed Mar. 1, 2013 for Chinese patent application No. 200680021083.6, a counterpart foreign application of U.S. Appl. No. 11/917,666, 6 pages.

Translated Japanese Office Action mailed Nov. 16, 2012 for Japanese patent application No. 2008-511846, a counterpart foreign application of US patent No. 8,105,941, 5 pages.

Final Office Action for U.S. Appl. No. 11/917,666, mailed on Jan. 11, 2013, Yongli Huang, "Micro-Electro-Mechanical Transducer Having an Insulation Extension", 20 pages.

Non-Final Office Action for U.S. Appl. No. 13/349,436, mailed on Jan. 23, 2013, Yongli Huang, "Through-Wafer Interconnection", 9 pages.

Non-Final Office Action for U.S. Appl. No. 13/349,436, mailed on Nov. 19, 2012, Yongli Huang, "Through-Wafer Interconnection", 6 pages.

Translated Chinese Office Action mailed Jun. 19, 2013 for Chinese patent application No. 200680021083.6, a counterpart foreign application of U.S. Appl. No. 11/917,666, 9 pages.

Translated Chinese Office Action mailed Sep. 12, 2013 for Chinese patent application No. 200680025783.2, a counterpart foreign application of US patent No. 8,105,941, 14 pages.

Office action for U.S. Appl. No. 13/568,697, mailed on Aug. 12, 2013, Huang, "Micro-Electro-Mechanical Transducers ", 12 pages.

Non-Final Office Action for U.S. Appl. No. 13/349,436, mailed on Aug. 2, 2013, Yongli Huang, "Through-Wafer Interconnection", 10 pages.

\* cited by examiner

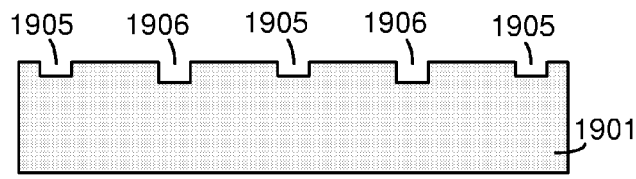
FIG. 19.1
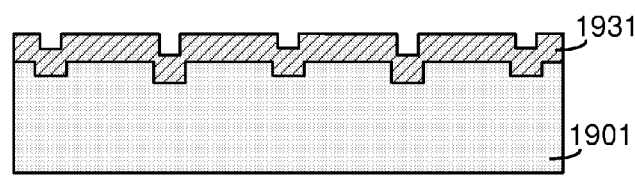
FIG. 19.2
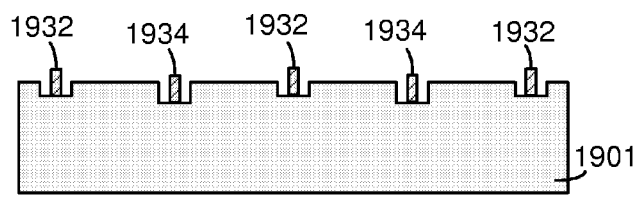
FIG. 19.3
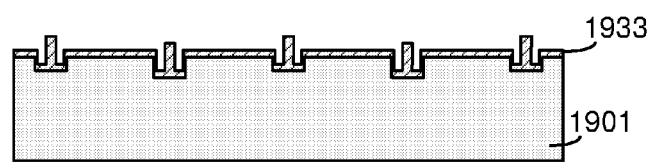
FIG. 19.4
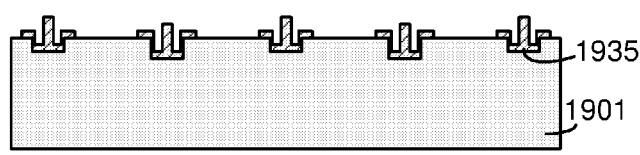
FIG. 19.5

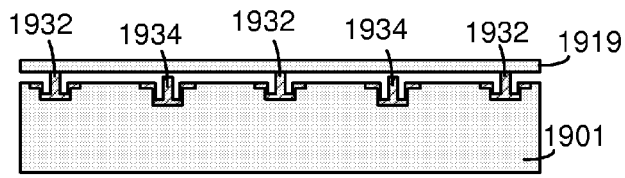
FIG. 19.6
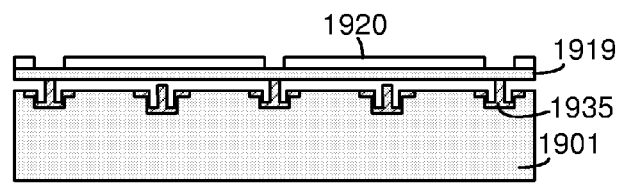
FIG. 19.7
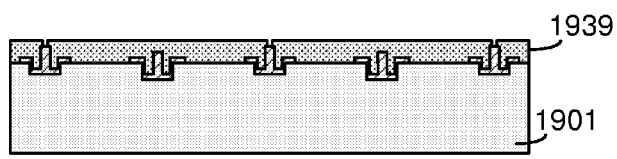
FIG. 19.6a
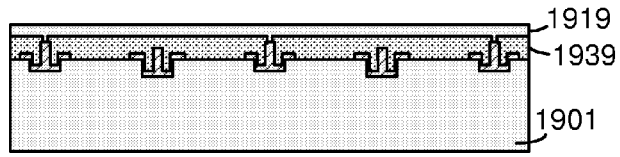
FIG. 19.7a
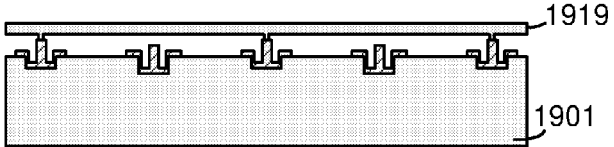
FIG. 19.8a
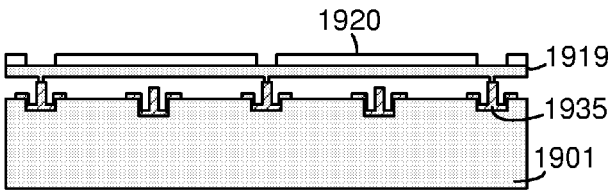
FIG. 19.9a

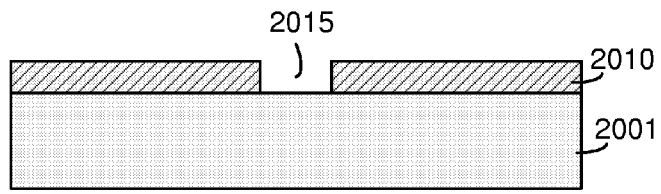
FIG. 20.1
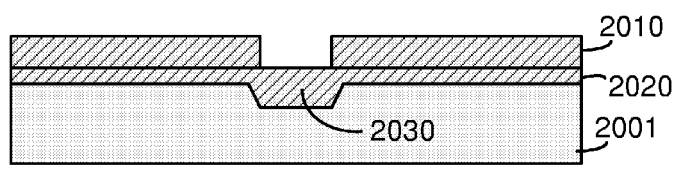
FIG. 20.2
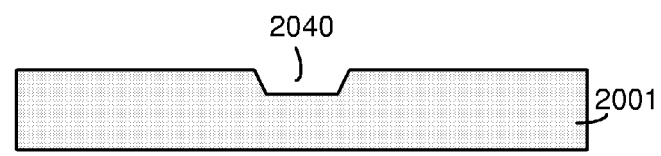
FIG. 20.3
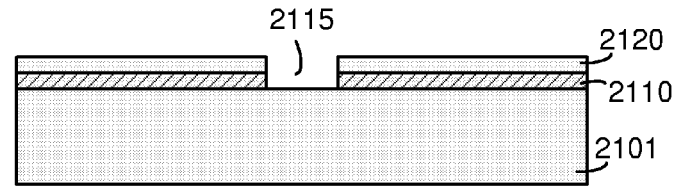
FIG. 21.1
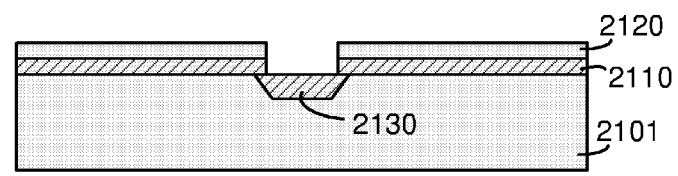
FIG. 21.2
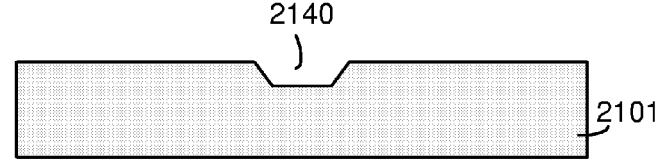
FIG. 21.3

FIG. 22.1
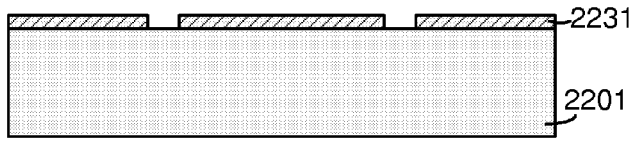
FIG. 22.2
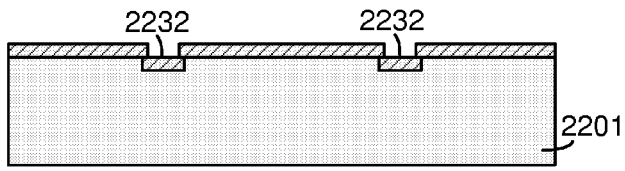
FIG. 22.3
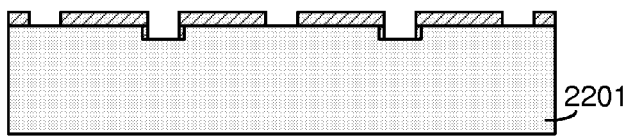
FIG. 22.4
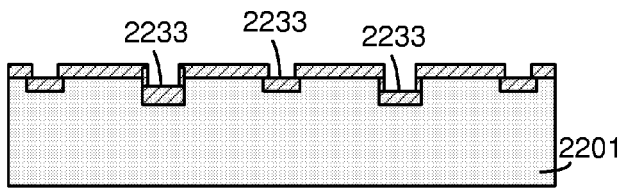
FIG. 22.5
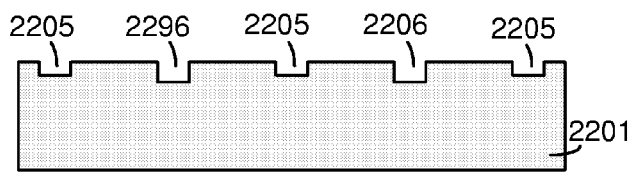

FIG. 23.1
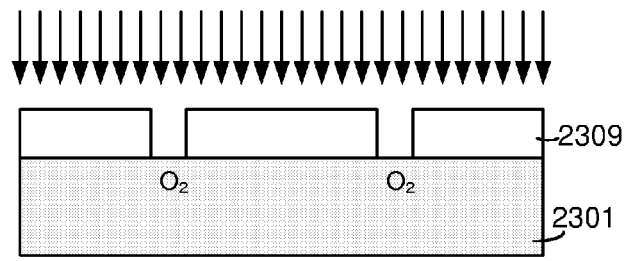
FIG. 23.2
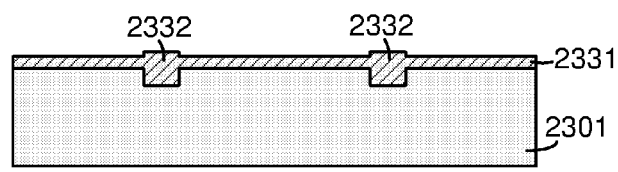
FIG. 23.3
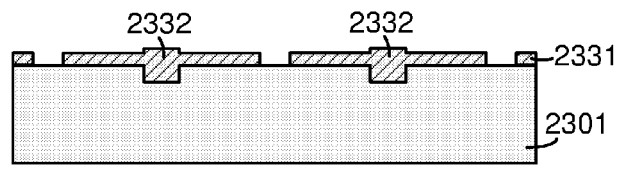
FIG. 23.4
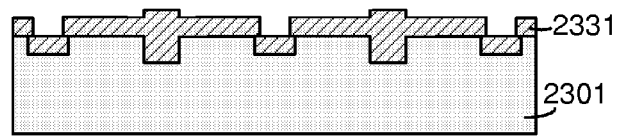
FIG. 23.5
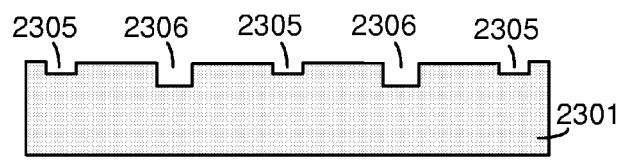

FIG. 24.1
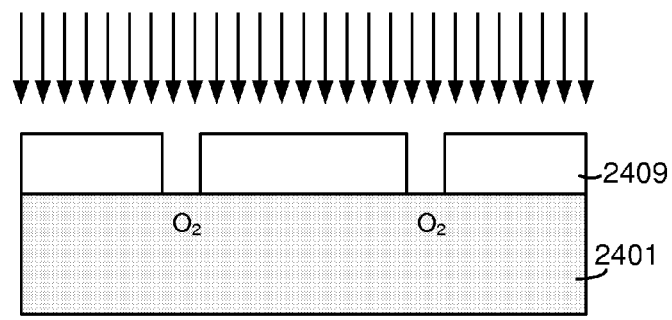
FIG. 24.2
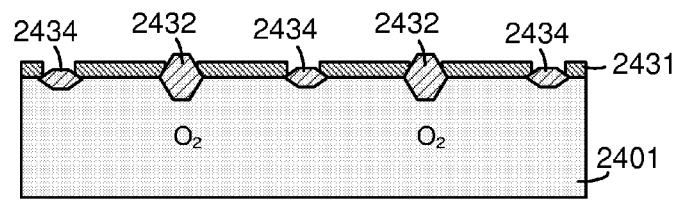
FIG. 24.3
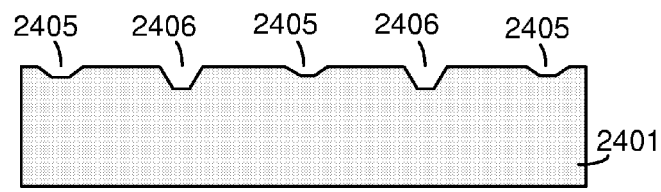

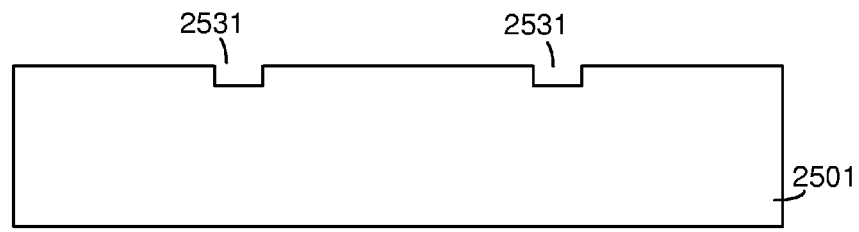
FIG. 25.1
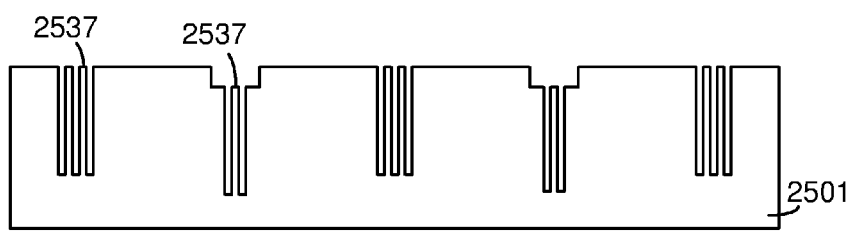
FIG. 25.2
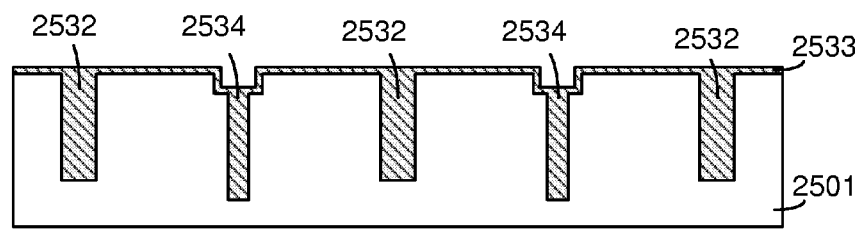
FIG. 25.3
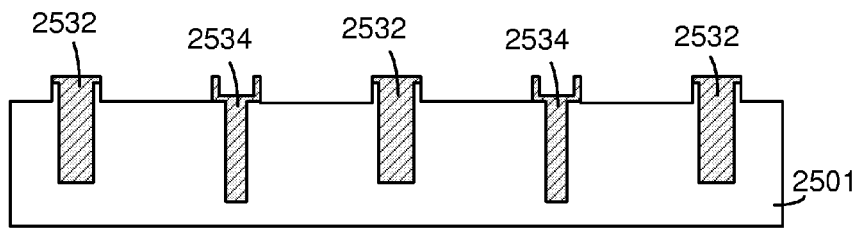
FIG. 25.4

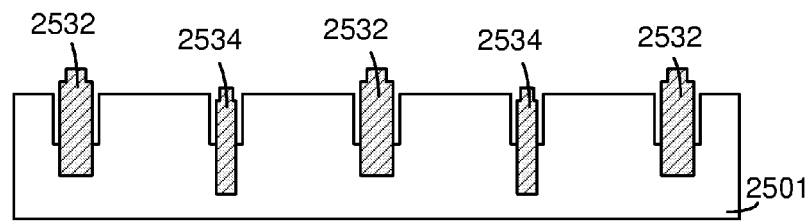
FIG. 25.5
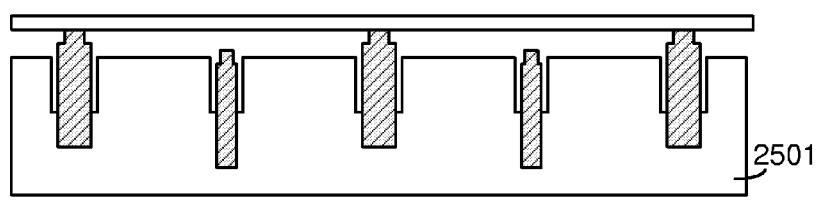
FIG. 25.6
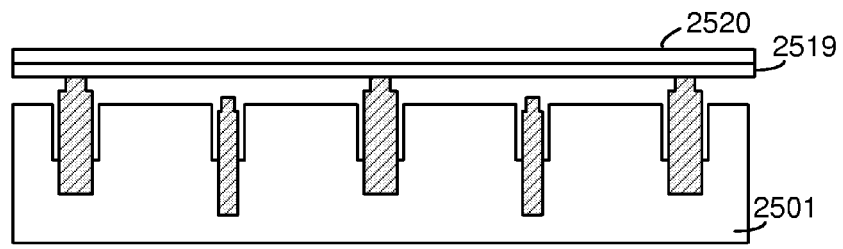
FIG. 25.7

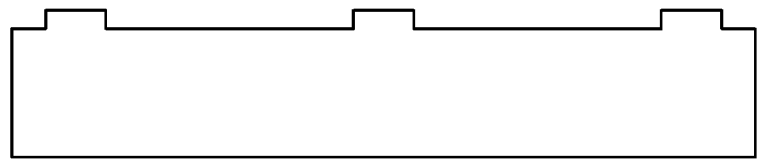
FIG. 25.1a
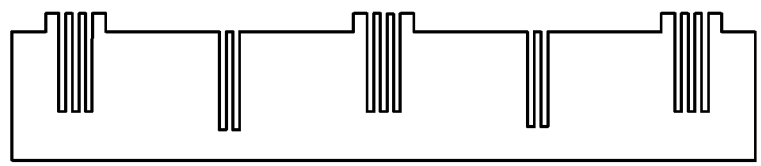
FIG. 25.2a
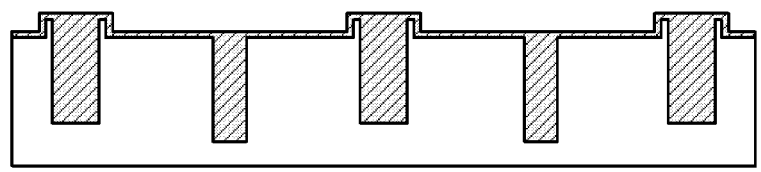
FIG. 25.3a
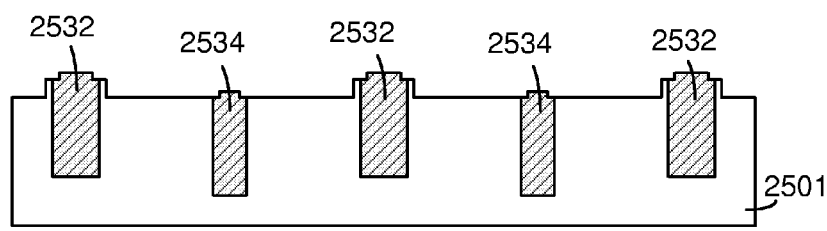
FIG. 25.4a

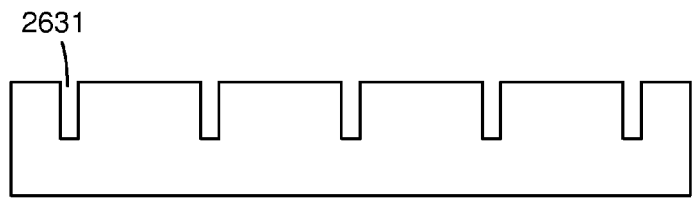
FIG. 26.1
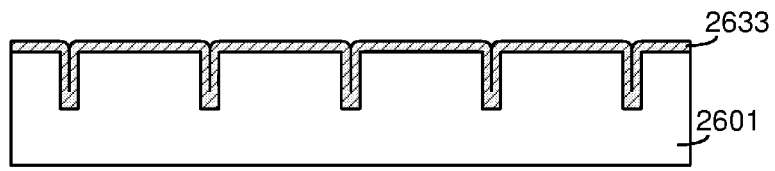
FIG. 26.2
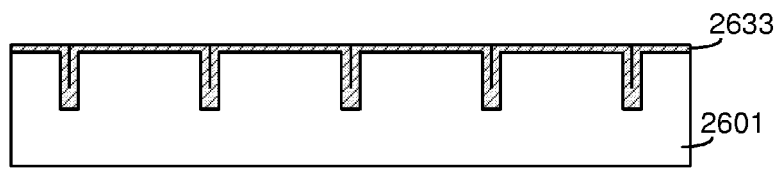
FIG. 26.3
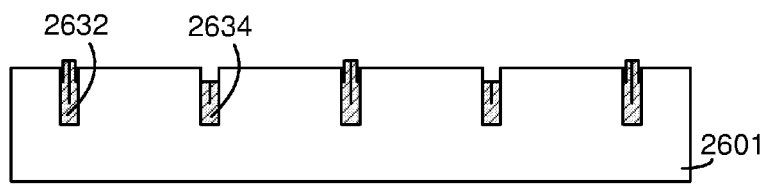
FIG. 26.4

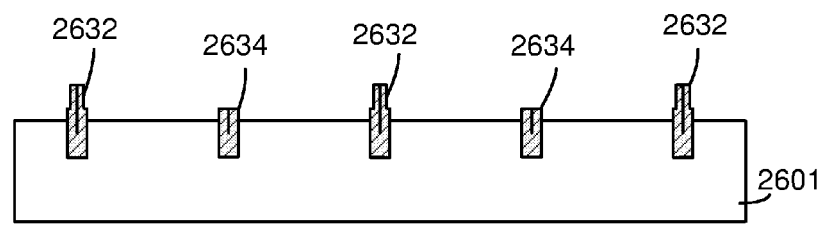
FIG. 26.5
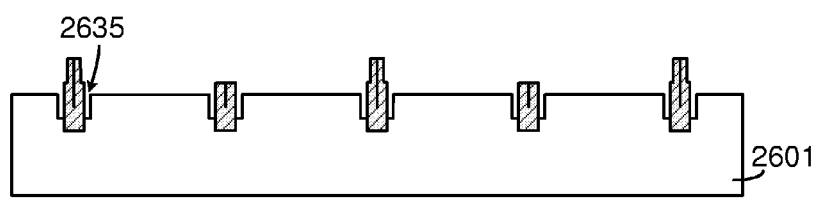
FIG. 26.6
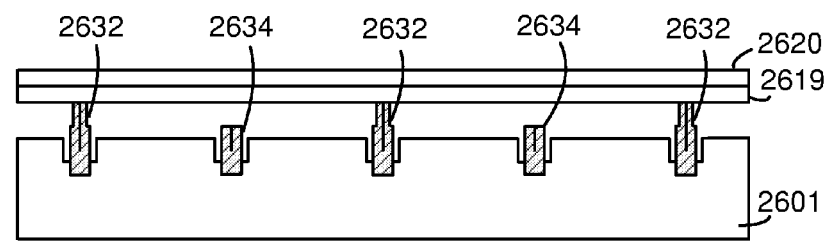
FIG. 26.7

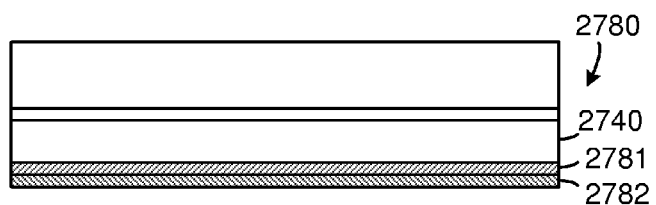
FIG. 27.1
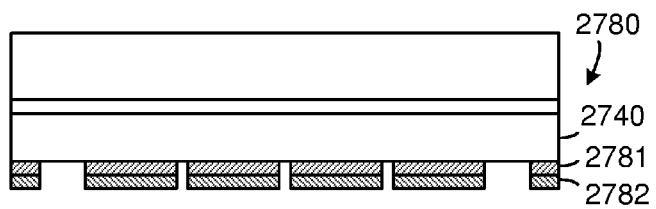
FIG. 27.2
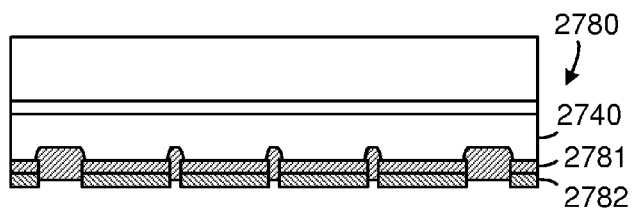
FIG. 27.3
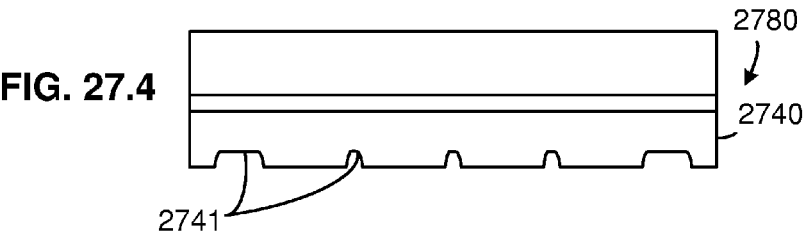
FIG. 27.4

FIG. 27.5
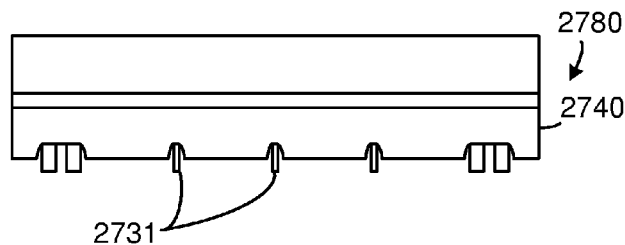
FIG. 27.6
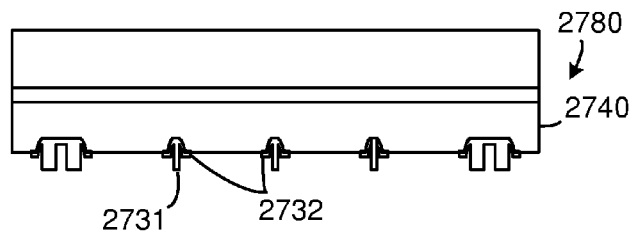
FIG. 27.7
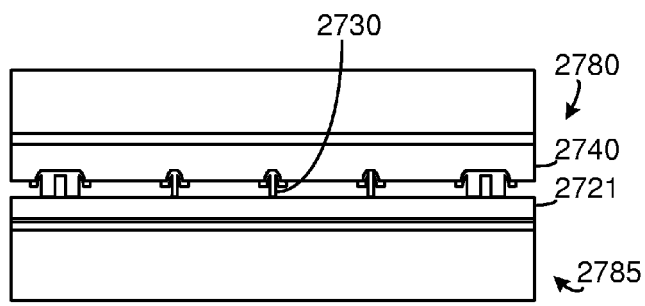
FIG. 27.8
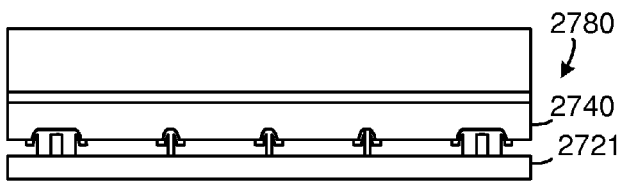

FIG. 27.9
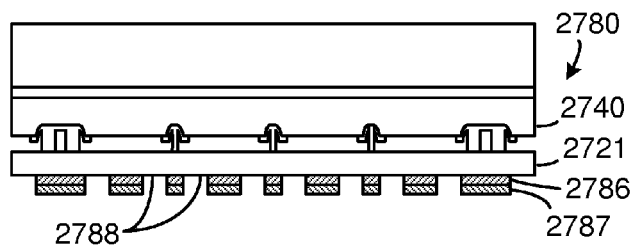
FIG. 27.10
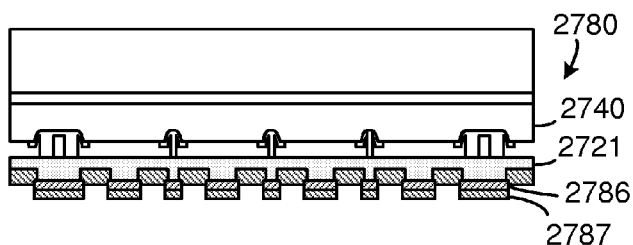
FIG. 27.11
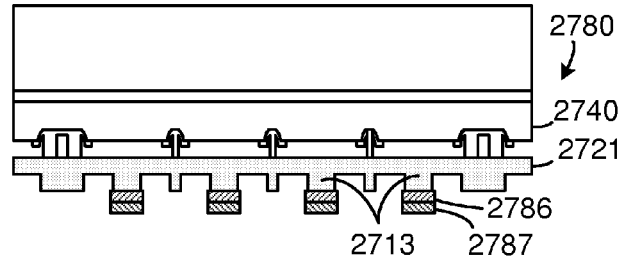
FIG. 27.12
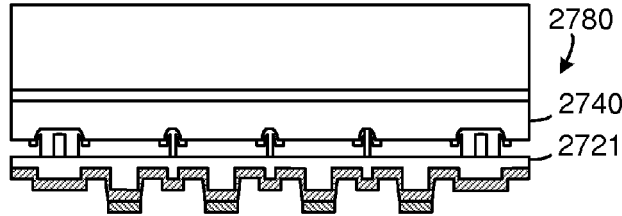

FIG. 27.13
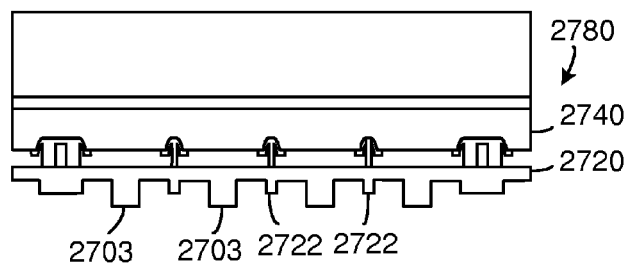
FIG. 27.14
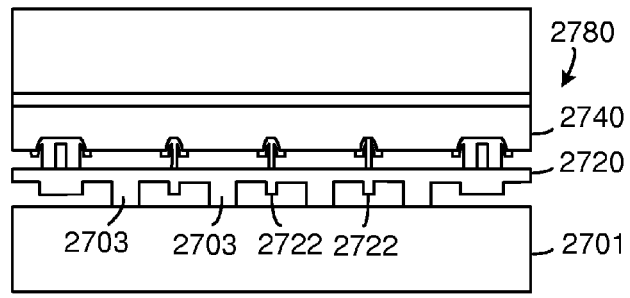
FIG. 27.15
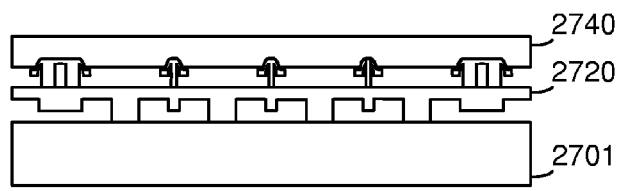
FIG. 27.16
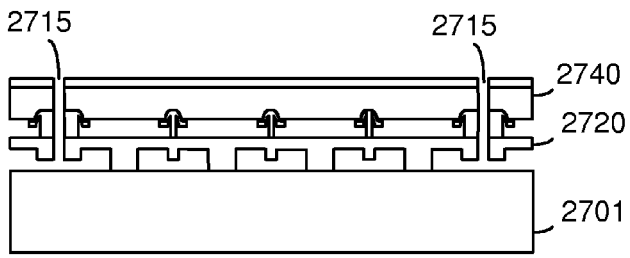

MICRO-ELECTRO-MECHANICAL TRANSDUCER HAVING AN INSULATION EXTENSION

This application claims priority from U.S. Provisional Application Ser. No. 60/692,038, filed Jun. 17, 2005; Ser. No. 60/705,606, filed Aug. 3, 2005; and Ser. No. 60/744,242, filed Apr. 4, 2006, which applications are incorporated herein by reference in their entirety.

This application further incorporates herein by reference in entirety the following:

International Application (PCT) No. PCT/IB2006/051567, entitled METHODS FOR FABRICATING MICRO-ELECTRO-MECHANICAL DEVICES, filed on May 18, 2006;

International Application (PCT) No. PCT/IB2006/051568, entitled MICRO-ELECTRO-MECHANICAL TRANSDUCERS, filed on May 18, 2006; and International Application (PCT) No. PCT/IB2006/051569, entitled MICRO-ELECTRO-MECHANICAL TRANSDUCERS, filed on May 18, 2006.

TECHNICAL FIELD

The present invention relates to micro-electro-mechanical devices that have a movable mechanical part for energy transformation, particularly to micromachined ultrasonic transducers (MUT) such as capacitive micromachined ultrasonic transducers (cMUT).

BACKGROUND ART

Micro-electro-mechanical transducers usually share a common feature which includes a movable mechanical part used for energy transformation. One example of such micro-electro-mechanical transducers is micromachined ultrasonic transducers (MUT). An ultrasound transducer performs a chain of energy transformation to realize its function of a transducer. In its receiving mode, the acoustic energy of ultrasound waves propagating in a medium where the transducer is placed is transformed to mechanical energy of a movable part (conventionally a vibrating membrane) in the transducer. The motion of the movable part is then transformed to a detectable electromagnetic (usually electrical) signal. In its transmitter mode, the reverse chain of energy transformation takes place.

Various types of ultrasonic transducers have been developed for transmitting and receiving ultrasound waves. Ultrasonic transducers can operate in a variety of media including liquids, solids and gas. These transducers are commonly used for medical imaging for diagnostics and therapy, biochemical imaging, non-destructive evaluation of materials, sonar, communication, proximity sensors, gas flow measurements, in-situ process monitoring, acoustic microscopy, underwater sensing and imaging, and many others. In addition to discrete ultrasound transducers, ultrasound transducer arrays containing multiple transducers have been also developed. For example, two-dimensional arrays of ultrasound transducers are developed for imaging applications.

Compared to the widely used piezoelectric (PZT) ultrasound transducer, the MUT has advantages in device fabrication method, bandwidth and operation temperature. For example, making arrays of conventional PZT transducers involves dicing and connecting individual piezoelectric elements. This process is fraught with difficulties and high expenses, not to mention the large input impedance mismatch problem presented by such elements to transmit/receiving electronics. In comparison, the micromachining techniques used in fabricating MUTs are much more capable in making such arrays. In terms of performance, the MUT demonstrates a dynamic performance comparable to that of PZT transducers. For these reasons, the MUT is becoming an attractive alternative to the piezoelectric (PZT) ultrasound transducers.

Among the several types of MUTs, the capacitive micromachined ultrasonic transducer (cMUT), which uses electrostatic transducers, is widely used. FIG. 1 shows a cross-sectional view of a basic structure of a prior art cMUT. The cMUT 10 of FIG. 1 is built on a substrate 11. Each cMUT cell has a parallel plate capacitor consisting of a rigid bottom electrode 12 and a top electrode 14 residing on or within a flexible membrane 16 that is used to transmit or receive an acoustic wave in the adjacent medium. The flexible membrane 16 in each cell is supported by the anchor 18. The membrane 16 is spaced from the substrate 11 and the top electrode 12 to define a transducing space 19 therebetween. A DC bias voltage is applied between the electrodes 12 and 14 to deflect the membrane 16 to an optimal position for cMUT operation, usually with the goal of maximizing sensitivity and bandwidth. During transmission an AC signal is applied to the transducer. The alternating electrostatic force between the top electrode and the bottom electrode actuates the membrane 16 in order to deliver acoustic energy into the medium (not shown) surrounding the cMUT 10. During reception the impinging acoustic wave vibrates the membrane 16, thus altering the capacitance between the two electrodes. An electronic circuit detects this capacitance change.

For proper operation, electrical insulation between the two electrodes 12 and 14 is needed. One basic form of such insulation is provided by the anchor 18, which can be made of an insulating material, and at the same time provides support between the two electrodes 12 and 14. In addition to the anchor 18, another insulation layer (not shown) may also placed between the two electrodes 12 and 14 of the cMUT 10 to prevent electric shorting during transducer operation. In general, the separation gap of the two cMUT electrodes 12 and 14 affects transduction performance of the cMUT, while the thickness of the insulate layer and height of the anchor 18 affect the breakdown voltage and the parasitic capacitance of the cMUT transducer, in a competitive manner. Usually, a smaller separation gap is desired for better transduction performance of the cMUT, while a thicker insulation layer and a taller anchor are desired for increasing the breakdown voltage and decreasing the parasitic capacitance. Therefore, the cMUT design is often a trade-off between these two competing factors with a compromise to the cMUT performance.

Due to the importance of these MUT devices, it is desirable to improve the technology in terms of performance, functionality, and manufacturability in general, and to optimize transduction performance, breakdown voltage and parasitic capacitance reduction in particular.

SUMMARY OF THE INVENTION

This patent application discloses a micro-electro-mechanical transducer (such as a cMUT) having two conductive layers (e.g., electrodes) separated by an insulator with an insulation extension. The two conductive layers define a transducing gap therebetween. The insulator has an insulating support disposed generally between the two conductive layers and an insulation extension extending into at least one of two conductive layers. The use of the insulation extension increases the effective insulation without having to increase the transducing gap. This patent application also discloses methods for fabricating the micro-electro-mechanical transducer. The inventive techniques may be used in both conventional membrane-based cMUTs and cMUTs having embedded springs transporting a rigid top plate.

In one embodiment, the host conductive layer (the conductive layer into which the insulation extension is extended) is thicker than the insulation extension such that the insulation extension is contained in the conductive layer. The conductive layer may include a base conductive layer and a supplemental conductive layer having conductivity significantly higher than that of the base conductive layer. The two layers may be formed on a silicon wafer with different doping levels. In one embodiment, the base conductive layer is a silicon layer and the supplemental conductive layer is a metal layer.

In one embodiment, the insulation extension extends into the conductive layer(s) by a depth that measures at least 25% of the transducing gap, thus significantly increasing the effective insulation without increasing the transducing gap.

The insulating support and the insulation extension may be formed of either the same or any combination of different insulating materials. The insulating support may be either separated or connected to the insulation extension.

In one embodiment, the insulation extension is disposed in a cavity formed in the host conductive layer. The insulation extension may be a solid material either completely filling the cavity or partially filling the cavity leaving a partial void therein.

The insulation extension may include two extension ends, a first extension end extending into the first conductive layer and a second extension end extending into the second conductive layer. The two extension ends may have either the same or different insulating materials.

In one embodiment, the insulation extension is located at a position where the two conductive layers are most likely to contact or come close to contact each other during operation. A motion stopper extending partially across the transducing gap to limit the maximum transducing distance may also be used.

The micro-electro-mechanical transducer in accordance with the present invention can be a capacitive micromachined ultrasonic transducer, wherein the first conductive layer serves as a bottom electrode and the second conductive layer serves as a movable top electrode. A conductive substrate such as a silicon wafer may serve as the bottom electrode. The second conductive layer may have a resilient membrane supported by the insulating support.

According to one aspect of the present invention, the insulation extension is incorporated in a micro-electro-mechanical transducer having embedded springs. The transducer comprises: (1) a substrate; (2) a middle spring layer placed over the substrate, the substrate and the middle spring layer defining a cavity therebetween, the cavity being bordered by a sidewall, wherein the middle spring layer extends from the sidewall to cover the cavity; (3) an insulating connector on the middle spring layer; (4) a top plate placed over the insulating connector, which separates the top plate from the middle spring layer to define a transducing gap below the top plate; and (5) an insulation extension extending beyond the transducing gap.

In one embodiment, the top plate comprises a conductive layer and the insulation extension extends into the conductive layer. For example, the top plate may have a silicon/polysilicon layer, and the insulation extension extends into the silicon/polysilicon layer. For a more effective electrode, the top plate may further include a metal layer.

In another embodiment, the middle spring layer comprises a conductive layer and the insulation extension extends into the conductive layer. Alternatively, the substrate may be conductive and the insulation extension extends into the conductive substrate.

The micro-electro-mechanical transducer having embedded springs may be a capacitive micromachined ultrasonic transducer having a bottom electrode and a top electrode. The bottom electrode may be part of the substrate and/or the middle spring, while the top electrode may be a part of the top plate. The sidewall of the substrate may be conductive, and the bottom electrode may include at least a part of the sidewall of the substrate. The bottom electrode may also include a separate conductive layer deposited on the middle spring layer or in the substrate.

In one embodiment, the top plate is significantly more rigid than the middle spring layer and is substantially unbent when transported by the vertical displacement of the insulating connectors. The maximum vertical displacement the top plate can be transported through the transducing space may be limited by a motion stopper.

In another embodiment of the present invention, a capacitive micromachined ultrasonic transducer (cMUT) comprises: (1) a lower layer including a substantially static substrate and serving as a bottom electrode; (2) a top layer including a membrane and serving as a top electrode, the membrane being adapted for vibrating in relation to the static substrate a transducing excitation, the top layer and the lower layer defining a transducing gap therebetween; and (3) an insulator having a main portion and an insulation extension, the main portion being generally disposed between and supporting the lower layer and the top layer, and the insulation extension extending into at least one of the lower layer and the top layer.

In one embodiment, at least one of the lower layer and the top layer has a conductive layer thicker than the insulation extension such that the insulation extension is contained within the conductive layer.

Another aspect of the present invention relates to a method for fabricating a micro-electro-mechanical transducer having two electrodes separated by an insulator with an insulation extension. The method comprises the steps of: (1) forming a recess on a major surface of a first conductive layer; (2) forming a standing feature of an insulating material, the standing feature extending from the recess to a free end above the major surface of the first wafer material; and (3) placing a second conductive layer over the free end of the standing feature.

The first conductive layer may comprise a silicon/polysilicon layer. The step of forming a recess may comprise a direct etching process, a differential oxidation process, or any combination thereof. The step of forming the standing feature may comprise growing an insulation layer over the recess, and patterning and etching the insulation layer. The step of placing the second conductive layer over the free end of the standing feature may comprise bonding an SOI wafer to the free end of the standing feature and etching back the SOI wafer to leave a desired portion of the SOI layer on the standing feature. The step of placing the second conductive layer may further comprise depositing a metal layer over the remaining layer of the SOI wafer. The desired portion of the SOI wafer remaining on the standing feature may comprise a silicon/polysilicon layer which forms at least part of the second conductive layer. In one embodiment, the desired portion of the SOI layer remaining on the standing feature provides a membrane layer adapted for vibrating in relation to the first conductive layer upon a suitable transducing excitation. Instead of using an SOI wafer, a wafer carrying a functional layer such as a nitride, oxide, metal, parylene or other polymer layer to serve as a desired membrane layer can be used.

In one embodiment of the above method, the step of placing the second conductive layer over the free end of the standing feature comprises: (1) depositing a sacrificial layer over the first conductive layer and the standing feature; (2) depositing a functional layer over the sacrificial layer; and (3) removing the sacrificial layer to leave the functional layer over the free end of the standing feature. The step of placing the second conductive layer may further comprise depositing a metal layer over the functional layer. The functional layer may include a silicon/polysilicon layer which forms at least part of the second conductive layer. The functional layer on the standing feature may be a membrane layer adapted for vibrating in relation to the first conductive layer upon a suitable transducing excitation.

Another method for fabricating a micro-electro-mechanical transducer having two electrodes separated by an insulator with an insulation extension comprises the steps of: (1) forming a patterned trench over a major surface of a substrate by removing material of the substrate, wherein the patterned trench comprises thin lines of unremoved material of the substrate; (2) oxidizing the thin lines of unremoved material of the substrate in the patterned trench such that the patterned trench constitutes an insulator; (3) patterning and etching the major surface of the silicon/polysilicon substrate such that the insulator in the trench having a top end standing above the substrate; and (4) placing a top conductive layer over the top end of the insulator.

An alternative method for fabricating a similar micro-electro-mechanical transducer comprises the steps of: (1) forming a trench over a major surface of a substrate by removing material of the substrate; (2) filling the trench with an insulating material; (3) patterning and etching the major surface of the silicon/polysilicon substrate such that the insulating material in the trench having a top end standing above the substrate; and (4) placing a top conductive layer over the top end of the insulator.

The method is also used for incorporating the insulation extension in accordance with the present invention in a micro-electro-mechanical transducer having embedded springs. An exemplary method for fabricating such a transducer comprises the steps of: (1) providing a top plate, a middle spring layer and a substrate; (2) forming a standing feature of an insulating material on a major surface of a host layer, which may be either the top plate or the middle spring layer, wherein the standing feature extends from a point below the major surface to a free end beyond the major surface; and (3) joining the top plate, the middle spring layer and the substrate, such that the top plate and the middle spring layer are connected by the standing feature at the free end thereof, and the middle spring layer is connected to the substrate at an opposing side. In the resultant transducer, the substrate and the middle spring layer define a cavity therebetween, the cavity is bordered by a sidewall, and the middle spring layer extends from the sidewall to cover the cavity.

In one embodiment, the host layer comprises a silicon/polysilicon layer, and the step of forming the standing feature comprises (1) forming a recess on a major surface of the silicon/polysilicon layer; and (2) forming the standing feature by introducing an insulating material over the recess. Alternatively, the step of forming the standing feature comprises the steps of: (1) forming a patterned trench over the silicon/polysilicon layer by removing silicon/polysilicon material, wherein the patterned trench comprises thin lines of unremoved material of the silicon/polysilicon layer; (2) oxidizing the thin lines of unremoved material of the silicon/polysilicon layer in the patterned trench such that the patterned trench contains an electrically nonconductive structure; and (3) patterning and etching the silicon/polysilicon layer to form the standing feature from the electrically nonconductive structure in the trench. Instead of using a patterned trench, a simple trench (without fine internal structures such as thin lines of unremoved material) may be formed and filled using an insulating material.

The foregoing and other features and advantages will become more apparent from the following detailed description of several embodiments, which proceeds with reference to the accompanying figures.

DESCRIPTION OF DRAWINGS

FIGS. 19.1-19.9a show an exemplary process flow to incorporate insulation extensions of the present invention into a conventional membrane-based cMUT using wafer-bonding technique.

FIGS. 20.1-20.3 show an exemplary process for forming a recess on a surface of an oxidizable layer using oxidation process.

FIGS. 21.1-21.3 show another exemplary process for forming a recess on a surface of an oxidizable layer using oxidation process.

FIGS. 22.1-22.5 show another exemplary process for forming a recess pattern having different recess depths on a substrate using oxidation process.

FIGS. 23.1-23.5 show another exemplary process to fabricate a desired recess pattern on a silicon substrate using O2 implantation and oxidation process.

FIGS. 24.1-24.3 show another process to fabricate a desired recess pattern on a silicon substrate using O2 implantation and Local Oxidation of Silicon (LOCOS).

FIGS. 25.1-25.7 show an exemplary method to form very deep insulation extensions in a conventional cMUT with a flexible membrane surface.

FIGS. 26.1-26.7 show another method to form deep insulation extensions by etching.

FIGS. 27.1-27.16 show a wafer-bonding process for fabricating an ESMUT having insulation extensions in accordance with the present invention.

DETAILED DESCRIPTION

Figure 1:
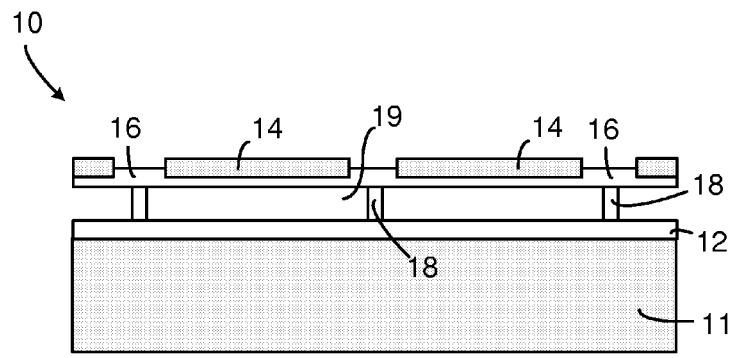
FIG. 1 shows a cross-sectional view of a basic structure of a prior art cMUT.

The micro-electro-mechanical transducer such as a capacitive micromachined ultrasonic transducer (cMUT) of the present invention will be described in detail along with the figures, in which like parts are denoted with like reference numerals or letters. The micro-electro-mechanical transducer may be fabricated using any suitable methods, particularly using the methods disclosed in the several patent applications identified herein.

The invention has been described below with reference to specific embodiments. In most cases, a cMUT structure is used to illustrate the invention. It is appreciated, however, that the present invention is not limited to cMUTs. It will be apparent to those skilled in the art that various modifications may be made and other embodiments can be used without departing from the broader scope of the inventions. Therefore, these and other variations upon the specific embodiments are intended to be covered by the present inventions. Those skilled in the art will recognize that various features disclosed in connection with the embodiments may be used either individually or jointly.

In this document, a conductive material is defined as one having a resistivity less than $1 \times 10^4$ Ω-cm. Silicon and polysilicon materials are therefore considered conductive materials in this context. A good conductive material preferably has a resistivity less than 1 Ω-cm. The terms 'insulation material', 'insulating material' and 'dielectric material' are used interchangeably unless noted otherwise, and are defined as one having a resistivity greater than $1 \times 10^4$ Ω-cm. A good insulation/insulating material preferably has a resistivity greater than $1 \times 10^8$ Ω-cm. An insulator generally comprises an insulating material but in special cases may include air and vacuum.

It is noted that the terms 'transducer' and 'transducing member' are used in a broad sense in the present description to not only include devices that perform both actuation and sensing functions but also include devices that perform either an actuation function or an sensing function. It is also noted that the term 'cantilever' is used in this description in a broad sense to describe a structure that has an anchored end, a resilient portion extending from the anchored, and to an exerting end to activate or move the resilient portion. A cantilever thus does not necessarily suggest a literal one-dimensional beam-like cantilever, but also includes similar structures have multibeams extending in different directions such as a bridge, or a crossbar, and most definitely also includes area or plane springs (two-dimensional 'cantilevers') in which the anchored end is an extended line which may be a closed perimeter of an area or a portion thereof, the resilient portion is an extended area, and the exerting end may be a single point, a small area, or an extended line (close ended, open-ended, or segmented).

In order to illustrate the present invention, certain aspects of the designs according to the prior art are first discussed in light of the present invention. It is noted that the discussion herein casts a hindsight on the prior art designs in light of the present invention for the purpose of clearer illustration.

For proper operation of a cMUT, electrical insulation between the two electrodes is needed. One basic form of such insulation is provided by anchors which at the same time also provide support between the two electrodes.

Figure 2:
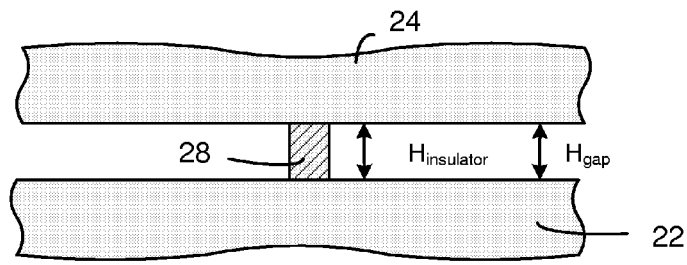
FIG. 2 shows an enlarged portion of a prior art cMUT to illustrate the relationship between the height of insulation anchor and the separation between the two electrodes.

FIG. 2 shows an enlarged portion of a prior art cMUT to illustrate the relationship between the height of insulation anchor and the separation between the two electrodes. As shown, $H_{insulator}$ is the height of anchor insulator 28 and is dictated or limited by the electrode separation gap $H_{gap}$ between the electrodes 22 and 24. In the configuration shown in FIG. 2, height of insulator $H_{insulator}$ is the same as the electrode separation gap $H_{gap}$.

Figure 3:
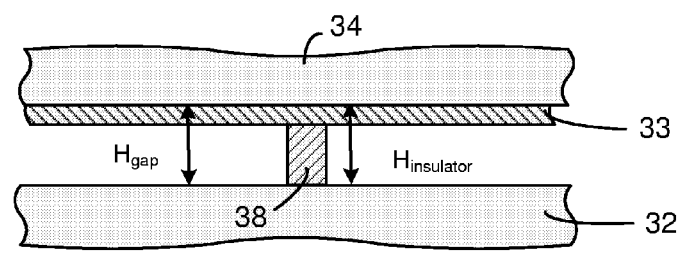
FIG. 3 shows an enlarged portion of another prior art cMUT to further illustrate the relationship between the height of insulation anchor and the separation between the two electrodes.

FIG. 3 shows an enlarged portion of another prior art cMUT to further illustrate the relationship between the height of insulation anchor and the separation between the two electrodes. In addition to anchor insulator 38, another insulation layer 33 is also placed between two electrodes 32 and 34 of the cMUT to prevent electric shorting between the electrodes 32 and 34 during transducer operation. Again, the total height of insulator $H_{insulator}$ is dictated or limited by the electrode separation gap $H_{gap}$ between the electrodes 32 and 34. In the configuration shown in FIG. 3, total height of insulator $H_{insulator}$ is the same as the electrode separation gap $H_{gap}$.

The separation gap $H_{gap}$ of the two electrodes in an electrostatic transducer such as cMUT affects transduction performance of the transducer. In general, smaller separation gap $H_{gap}$ results in better transduction performance. On the other hand, the height of insulator $H_{insulator}$ affects the breakdown voltage and the parasitic capacitance of the transducer. Usually, a thicker insulation layer and taller anchor (i.e., greater $H_{insulator}$) is desired for increasing the breakdown voltage and decreasing the parasitic capacitance. But because in conventional designs of electrostatic transducer $H_{insulator}$ is inherently dictated or limited by $H_{gap}$, there is often a trade-off between these two competitive factors with a compromise or limitation to the transducer performance.

The present invention is envisioned to eliminate the above limitation inherent to prior art designs of electrostatic transducers such as cMUT.

Figure 4:
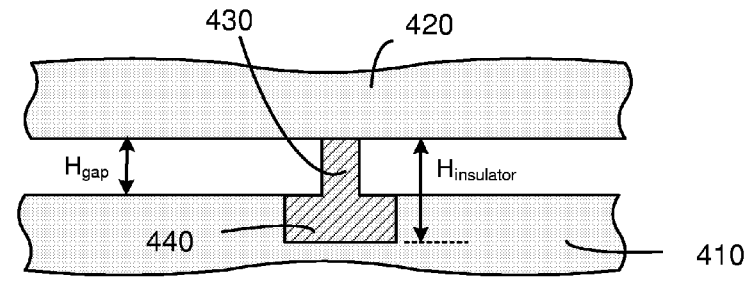
FIG. 4 shows an enlarged portion of an electrostatic transducer in accordance with the present invention.

FIG. 4 shows an enlarged portion of an electrostatic transducer in accordance with the present invention. The electrostatic transducer has the bottom electrode 410 and a top electrode 420 separated from each other by separation gap $H_{gap}$. The separation of the bottom electrode 410 the top electrode 420 defines a transducing gap therebetween. An insulating support portion 430 is disposed generally between the bottom electrode 410 and the top electrode 420. The electrostatic transducer further has an insulation extension 440 extending into the bottom electrode 410.

The above design changes the relationship between $H_{insulator}$ and $H_{gap}$. As shown, $H_{insulator}$ is the sum of the height of insulating support portion 430 and the thickness of the insulation extension 440. Although the height of insulating support portion 430 is still limited by the electrode separation gap $H_{gap}$, the thickness of the insulation extension 440 is free of such restriction and thus provides a degree of design freedom to increase the total insulator height $H_{insulator}$ without also increasing the electrode separation gap $H_{gap}$. Since the added insulation extension 440 does not affect the separation between two electrodes of 410 and 420, it can be freely designed to have any desired thickness to achieve the desired breakdown voltage and parasitic capacitance without scarifying the device transduction performance.

By decoupling insulator height $H_{insulator}$ from the electrode separation gap $H_{gap}$, the transducer performance can be improved by optimizing the transducer electrode separation $H_{gap}$, while at the same time the breakdown voltage and the parasitic capacitance can also be optimized without any trade-off between them. This novel design can be used in a variety of electrostatic transducers, and is particularly important to improve the performance of high frequency cMUTs.

As will be shown in the description of fabrication methods herein, the insulation extension 440 may be formed in the electrode 410 in a variety of ways. In one embodiment, a cavity is first formed in the electrode 410 and an insulating material is then introduced into the cavity to form the insulation extension 440. The insulating material may be a solid material completely filling the cavity, but may also be any other insulating material either completely filling the cavity or partially filling the cavity leaving a partial void therein.

The insulation extension 440 and the insulating support portion 430 may either be made of the same insulating material or any combination of different insulating materials. In the configuration shown in FIG. 4, the bottom electrode 410 is thicker than the insulation extension 440 such that the insulation extension 440 is contained within the bottom electrode 410. However, the insulation extension 440 may extend beyond the bottom electrode 410, particularly if the bottom electrode 410 is a part of a thicker combined layer that contains the insulation extension 440.

In another embodiment, the bottom electrode 410 may comprise multiple conductive layers or a conductive layer on a dielectric substrate. For example, the bottom electrode 410 may have a base conductive layer and a supplemental conductive layer. This may be the case when a silicon substrate is used as the base conductive layer and a supplemental conductive layer having a conductivity significantly higher than that of the silicon substrate (the base conductive layer) is used to make a more effective electrode. Examples of a supplemental layer include a polysilicon layer, a metal layer, or a contiguous part of the same silicon substrate but with a higher doping level. In such a case, the insulation extension 440 may extend beyond the supplemental layer and further into the silicon substrate.

The thickness of the insulation extension 440 extending into the bottom electrode 410 may be determined by design requirements for the optimization of breakdown voltage, parasitic capacitance and transduction performance. This extension thickness is essentially a design freedom unlimited in principle except by performance considerations. For example, in one embodiment, the insulation extension 440 may have a depth that measures at least 25% of the transducing gap to ensure noticeable improvement.

The insulation extension 440 is shown to be wider in its cross-sectional dimension than the insulation support portion 430. Such a configuration may be preferred for the purpose of optimizing breakdown voltage and parasitic capacitance without having too great a support area, but is not required.

Figure 4A:
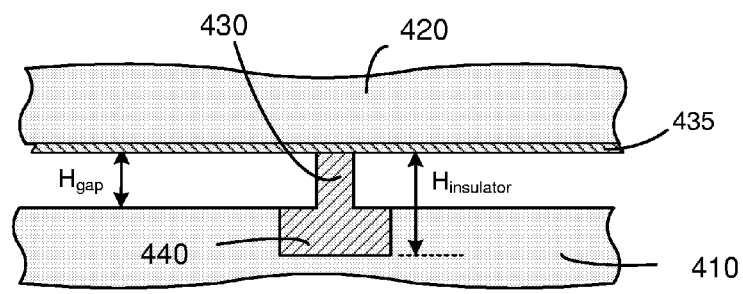
FIGS. 4a and 4b show two variations of the insulation extension concept shown in FIG. 4.
Figure 4B:
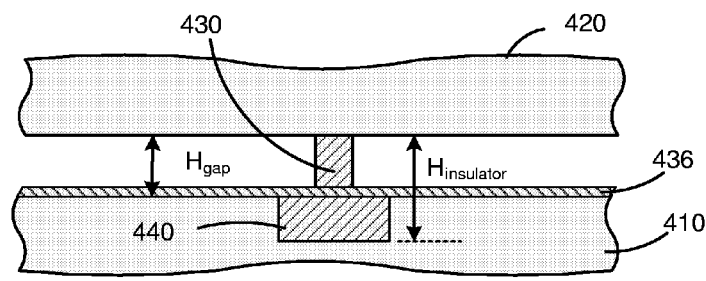

The insulation extension 440 and the insulating support portion 430 may be directly connected to each other as shown in FIG. 4 (and in some embodiments may even be portions of the same contiguous piece of an insulating material), or intervened by another insulation layer 435 for as shown in two alternative configurations in FIGS. 4a and 4b.

Figure 5:
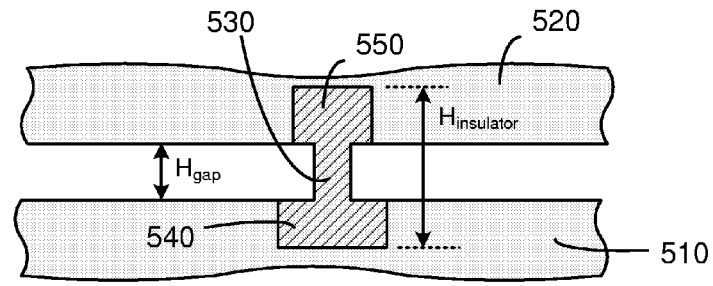
FIGS. 5-7 show additional variations of the insulation extension concept shown in FIG. 4.
Figure 6:
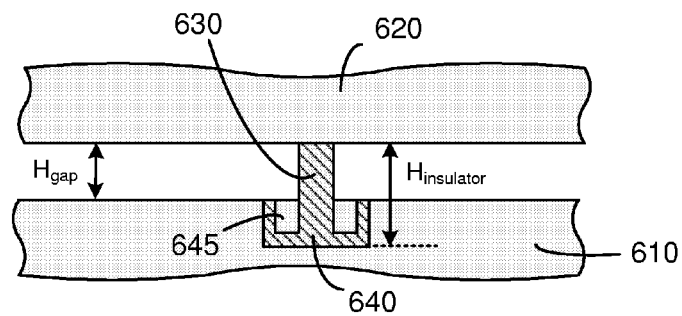
Figure 7:
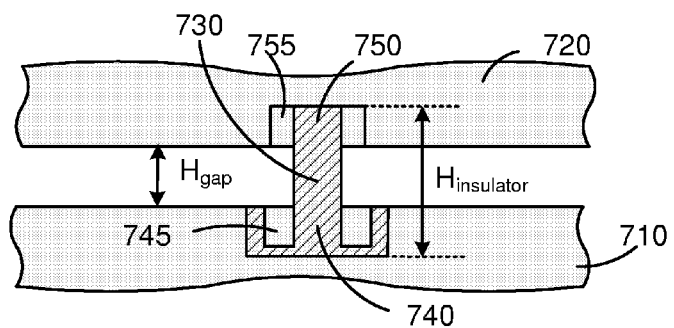

FIGS. 5-7 show variations of the concept shown in FIG. 4. In these figures, similar components are denoted using similar or the same reference numerals. FIG. 5 shows an electrostatic transducer similar to that of FIG. 4 except that the insulator in FIG. 5 has two insulation extensions 540 and 550, extending into the bottom electrode 510 and the top electrode 520, respectively. Similar to that in FIG. 4, bottom electrode 510 and top electrode 520 are separated from each other by separation gap $H_{gap}$. The separation of the bottom electrode 510 the top electrode 520 defines a transducing gap therebetween. An insulating support portion 530 is disposed generally between the bottom electrode 510 and the top electrode 520.

As shown, $H_{insulator}$ is the sum of the height of insulating support portion 530 and the thicknesses of the insulation extensions 540 and 550. For a given separation gap $H_{gap}$, the total height of the insulator $H_{insulator}$ may be optimized by adjusting the thickness of either insulation extension 540 or insulation extension 550, or both.

FIG. 6 shows another electrostatic transducer similar to that of FIG. 4 except that in FIG. 6 the insulation extension has a slightly more complex structure. The insulation extension in bottom electrode 610 includes a first portion 640 and a second portion 645, which may be made of different insulating materials. As shown, the first portion 640 of the insulation extension is structured to define certain voids (occupied by the second portion 645 as shown). The first portion 640 is contiguous with the insulation support portion 630, while the second portion 645 of the insulation extension occupies voids defined by the structured first portion 640. In one embodiment, the second portion 645 comprises air or sealed vacuum.

FIG. 7 shows another electrostatic transducer similar to that of FIG. 5 in having two insulation extensions extending into the bottom electrode 710 and the top electrode 720. The insulation extensions in FIG. 7, however, each has a slightly more complex structure than its counterpart in FIG. 5. The insulation extension in bottom electrode 710 includes a first portion 740 and a second portion 745, which may be made of different insulating materials. Similarly, the insulation extension in top electrode 720 includes a first portion 750 and a second portion 755. As shown, the first portions 740 and 750 of the insulation extensions are contiguous with the insulation support portion 730, while the second portions 745 and 755 of the insulation extensions each occupies voids defined by the first portions 740 and 750. In one embodiment, the second portions 745 and 755 each comprises air or sealed vacuum.

The above basic designs of insulation extensions may be embodied in a variety of micro-electro-mechanical transducers as illustrated below with reference to FIGS. 8-18 using cMUT as an example. In particular, it may be used in a capacitive micromachined ultrasonic transducer that comprises: (1) a lower layer including a substantially static substrate and serving as a bottom electrode; (2) a top layer including a membrane or a plate and serving as a top electrode, the membrane or plate being adapted for vibrating in relation to the static substrate a transducing excitation, the top layer and the lower layer defining a transducing gap therebetween; and (3) an insulator having a main portion and an insulation extension, the main portion being generally disposed between and supporting the lower layer and the top layer, and the insulation extension extending into at least one of the lower layer and the top layer.

It is appreciated that although a certain type of insulation extension configuration is used in these examples for the purpose of illustration, any other insulation extension configurations (such as those described above with references to FIGS. 4-7) within the general concept of the present invention can be used for equal or similar purposes.

Figure 8:
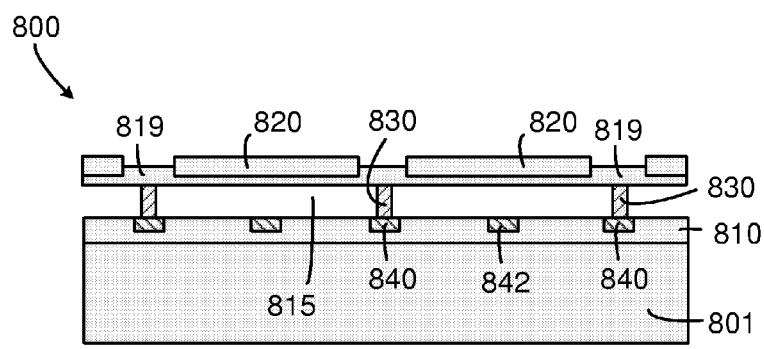
FIG. 8 is a cross-section view of a cMUT structure using an insulation extension in accordance with the present invention.

FIG. 8 is a cross-section view of a cMUT structure using an insulation extension in accordance with the present invention. The cMUT element 800 is built on a substrate wafer 801 and has a bottom electrode layer 810 and a membrane layer 819 carrying a top electrode layer 820. Insulating supports (anchors) 830 are disposed between the bottom electrode layer 810 and the membrane layer 819 (with the top electrode layer 820) to support the membrane layer 819, which is fixed or clamped at top ends of the insulating supports (anchors) 830. The membrane layer 819 and the bottom electrode layer 810 define a transducing gap 815. The membrane layer 819 vibrates in relation to the substrate through the transducing 815 upon receiving a transducing excitation to perform transducing function.

It is appreciated that in FIG. 8, as well as in other figures herein, the bottom electrode layer 810 is not required to be a separate layer from the substrate 801. In some embodiments, the substrate 801 and the bottom electrode 810 may be a single conductive layer which serves as the bottom electrode. In other embodiments, substrate 801 may be a conductive silicon substrate and the bottom electrode 810 a contiguous portion of the same substrate 801 but with a higher doping level.

The insulation extensions 840 and 842 are formed in bottom electrode layer 810 to extend the total insulator height. The insulation extensions 840 are each connected to a corresponding insulating supports (anchors) 830, while the insulation extensions 842 are not connected to an insulating support (anchor) but is positioned at a location where the top electrode 820 and the bottom electrode 810 are most likely to contact or come close to contact each other during operation of the transducer. Such positions are usually, but not always, near the middle of each cMUT cell defined by two opposing insulation sports (anchors) 830. The insulation extension 842 is, by way of illustration, positioned in the middle of the two insulation extensions 840. Any design of insulation extensions illustrated above may be used as a substitute of the insulation extensions 840 and 842 shown.

Figure 9:
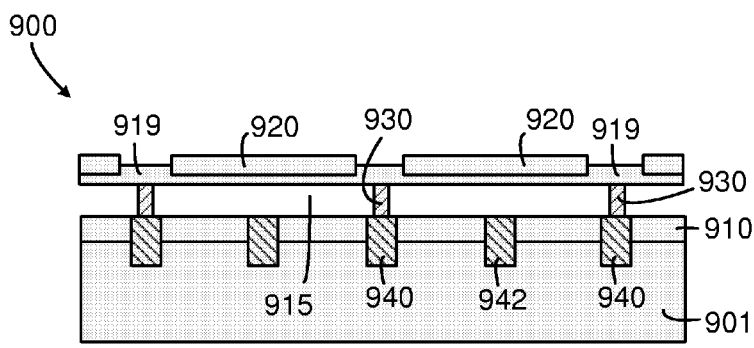
FIGS. 9-14 are cross-section views of variations of cMUT structures using an insulation extension in accordance with the present invention.

FIG. 9 is a cross-section view of another cMUT structure using an insulation extension in accordance with the present invention. The cMUT structure 900 is similar to the cMUT structure 800 shown in FIG. 8 except that insulation extensions 940 and 942 extend beyond the bottom electrode 910 into the substrate 901. This configuration may be benefiting when the substrate 901 itself is made of a material that is either conductive or not highly insulative. For example, the substrate 901 may be a silicon wafer which is considered conductive in the context of the present invention. The conductive substrate 901 functions as a part of the bottom electrode together with the bottom electrode layer 910 which is preferably more conductive than the substrate 901.

Figure 10:
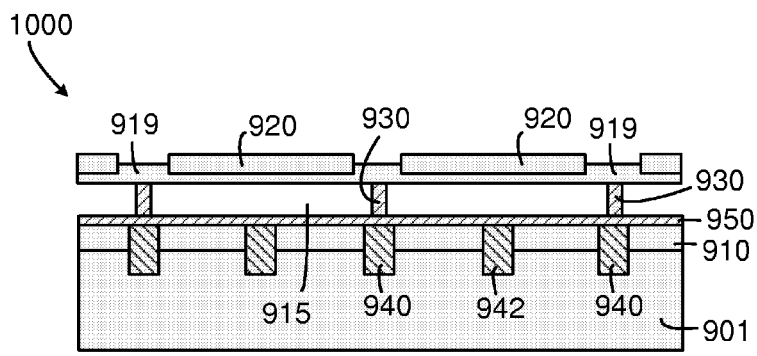

FIG. 10 is a cross-section view of another cMUT structure using an insulation extension in accordance with the present invention. The cMUT structure 1000 is similar to the cMUT structure 900 shown in FIG. 9 except that the cMUT structure 1000 further includes an insulation layer 950 between the insulating supports (anchors) 930 and the insulation extensions 940 and 942. It is appreciated that the insulation layer 950 may also be placed between the membrane layer 919 and the insulating supports (anchors) 930.

Figure 11:
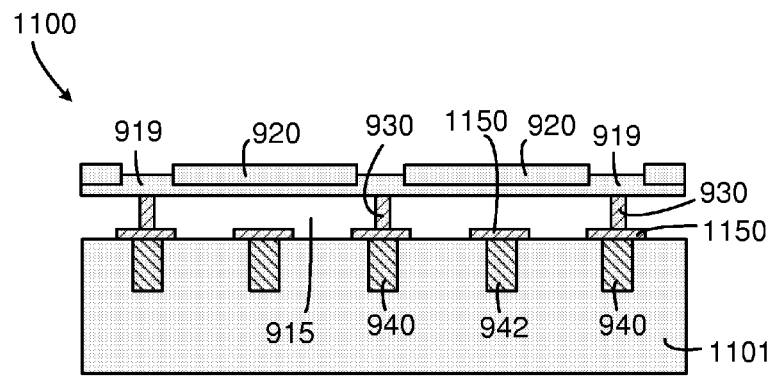

FIG. 11 is a cross-section view of another cMUT structure using an insulation extension in accordance with the present invention. The cMUT structure 1100 is similar to the cMUT structure 1000 shown in FIG. 10 except for the following differences: (1) the insulation layer 1150 is patterned in the cMUT structure 1100 to cover only areas above insulation extensions 940 and 942; and (2) conductive substrate 1101 alone functions as the bottom electrode without an additional conductive layer. One suitable material for conductive substrate 1101 is a doped silicon wafer.

Figure 12:
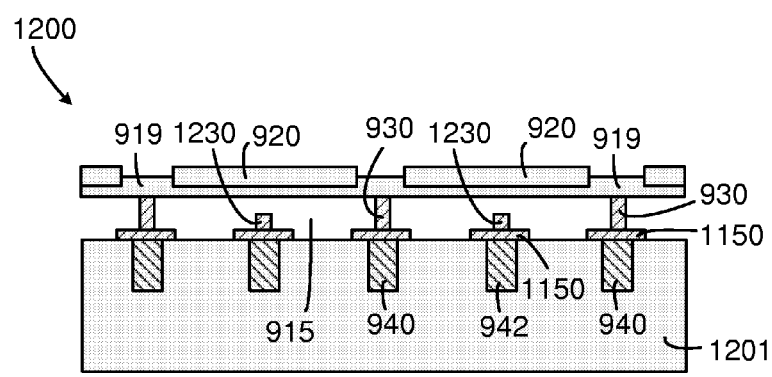

FIG. 12 is a cross-section view of another cMUT structure using an insulation extension in accordance with the present invention. The cMUT structure 1200 is similar to the cMUT structure 1100 shown in FIG. 11 except that the cMUT structure 1200 further includes motion stoppers 1230 placed above insulation extensions 942. As shown, unlike insulation extensions 940 which are placed below and connected to insulation supports (anchors) 930, insulation extensions 942 are placed near a middle of each cMUT cell where the electrodes are most likely to contact or come close to contact each other during operation. (In a particular configuration of FIG. 12, the bottom electrode comprises the conductive substrate 1201, while the top electrode 920 comprises a patterned conductive layer carried by the membrane layer 919). Motion stoppers 1230 placed at such locations help to limit the maximum displacement of the top electrode 920 in relation to the bottom electrode during operation and thus prevents direct shorting between the electrodes.

Figure 13:
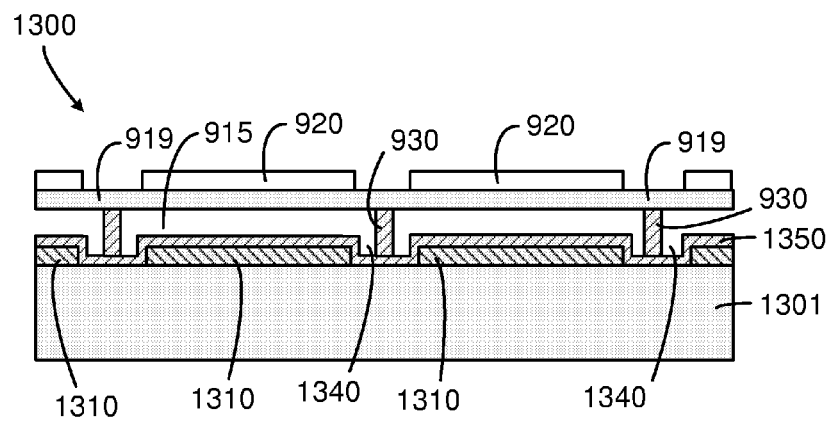

FIG. 13 is a cross-section view of the cMUT structure that achieves a similar effect of an insulation extension in accordance with the present invention. The cMUT structure 1300 is built on substrate 1301 and has a patterned bottom electrode layer 1310 placed over the substrate 1301. An insulation layer 1350 covers the top surface of the substrate 1301 and the bottom electrode 1310. The patterned bottom electrode layer 1310 defines voids 1340, which may serve as at least a part of the insulation extension if they contain sealed vacuum or air. In the particular example shown in FIG. 13, the voids 1340 are partially filled with insulation layer 1350. In this case, the remaining empty areas of the voids 1340 and the portions of the insulation layer 1350 filled in the voids 1340 together serve as insulation extensions.

The substrate 1301 may be made of insulation material, a conductive material, or a conductive material covered by an insulation material. The substrate 1301, if made of a conductive material, may also serve as at least a part of the bottom electrode.

Figure 14:
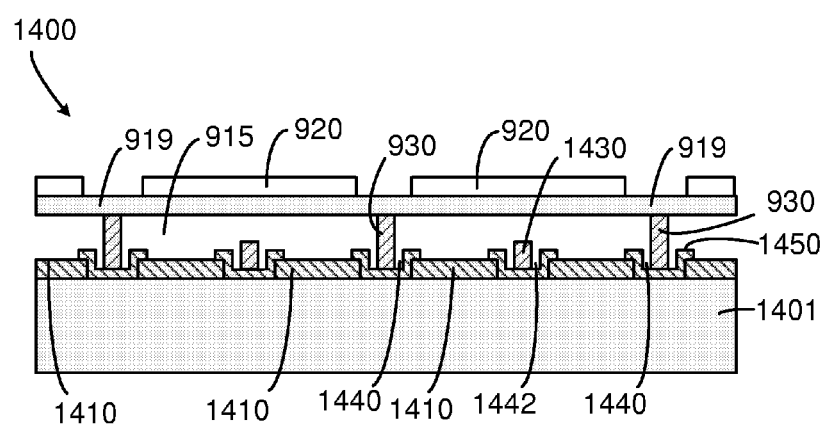

FIG. 14 is a cross-section view of another cMUT structure that achieves a similar effect of an insulation extension in accordance with the present invention. The cMUT structure 1400 is similar to the cMUT structure 1300 shown in FIG. 13 except that the cMUT structure 1400 further includes motion stoppers 1430 placed over additional insulation extensions 1442, and the insulation layer 1450 is patterned and does not cover large portions of the bottom electrodes 1410.

In addition to patterning the bottom electrode as shown in FIGS. 13-14 above, the top electrode may also be patterned such that the top electrode and the bottom electrode do not overlap with each other at certain selected locations such as near where the insulation supports (anchors) 930 are located and where the top electrode and the bottom electrode are most likely to contact or come close to contact each other during operation.

The insulation extension in accordance with the present invention may also be used in micro-electro-mechanical transducers having embedded springs as described in the several PCT patent applications referenced herein. In particular, the insulation extension may be used in a micro-electro-mechanical transducer having a movable mechanical part to transform energy. An exemplary transducer comprises: (1) a substrate; (2) a middle spring layer placed over the substrate, the substrate and the middle spring layer defining a cavity therebetween, the cavity being bordered by a sidewall, wherein the middle spring layer extends from the sidewall to cover the cavity; (3) an insulating connector on the middle spring layer; (4) a top plate placed over the insulating connector, which separates the top plate from the middle spring layer to define a transducing gap below the top plate; and (5) an insulation extension extending beyond the transducing gap.

Figure 15:
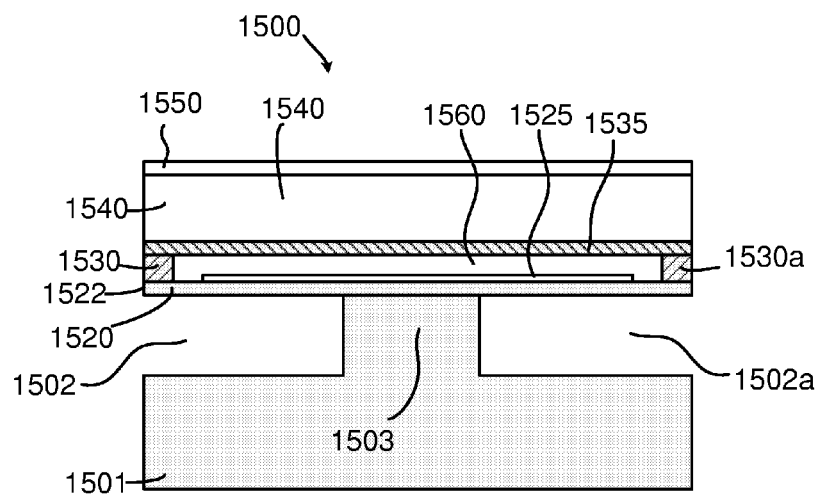
FIG. 15 is an enlarged view of a selected portion of an embedded spring micro-electro-mechanical transducer (ESMUT).

FIG. 15 is an enlarged view of a selected portion of an embedded spring micro-electro-mechanical transducer (ESMUT). The ESMUT portion 1500 is a part of a complete ESMUT element (not shown). The structure of the selected ESMUT portion 1500 provides a basis to understand the complete ESMUT element as described in the several PCT patent applications referenced herein.

For certain application such as an ESMUT with a high operation frequency, a full ESMUT element or device may use only one basic unit like ESMUT portion 1500. For other applications, it may be preferred to use a combination of multiple basic units shown in FIG. 15 and/or FIG. 16.

The ESMUT portion 1500 is built on a substrate 1501, on top of which there is a standing feature (referred to as 'sidewall anchor' hereinafter) 1503 having two sidewalls on two opposing sides bordering cavities 1502 and 1502a, respectively. The standing feature (sidewall anchor) 1503 may be an integrated part of the substrate 1501 formed as a result of forming the cavities 1502 and 1502a, but may also be an additional structure added onto a separate substrate. In one embodiment, for example, the sidewall anchor 1503 is part of the middle spring layer 1520. The substrate of 1501 may be made of either a nonconductive material or a conductive material such as silicon or polysilicon. In a configuration where the sidewall anchor 1503 is a separate structure, conductivity of the sidewall anchor 1503 may be the same as or different from that of the substrate 1501. For example, the substrate 1501 may be made of a nonconductive material while the sidewall anchor 1503 a conductive material such as metal, silicon or polysilicon.

The ESMUT structure shown also has the second cavity 1502a long the other side of sidewall anchor 1503. Depending on how and where the ESMUT portion 1500 is taken from the ESMUT element, the second cavity 1502a may either belong to a different and separate cavity, or just another portion of a same circular or extended cavity as the cavity 1502. The selected ESMUT portion 1500 also has a second connector 1530a in the other half. Again, depending on how and where the ESMUT portion 1500 is taken from the ESMUT element 1500, the second connector 1530a may either be a part of a different and separate connector, or just another portion of a same circular or extended connector as the connector 1530.

The ESMUT structure portion 1500 further has these components: (a) a middle spring layer 1520 which is preferably an elastic membrane; (b) a bottom electrode 1525 placed on the middle spring layer 1520, connectors 1530 and 1530a which stand on top of the middle spring layer 1520; (c) an insulation layer 1535 sitting over the connector 1530; (d) a top plate 1540 connected to the connectors 1530 and 1530a through an intervening insulation layer 1535; and (e) a top electrode 1550.

The bottom side of the top plate 1540 faces the top side of the middle spring layer 1520, and the bottom side of the middle spring layer 1520 faces the front side of the substrate wafer, whereby the connector 1530 stands out from the middle spring layer 1520 to define a transducing space 1560 below the top plate 1540. The transducing space 1560 is generally defined between the top plate layer 1540 and the top surface of the middle spring layer 1520 or the top surface of the sidewall anchor 1503, whichever is higher. Where there is an intervening layer between the top plate layer 1540 and the top surface of the middle spring layer 1520 or the top surface of the sidewall anchor 1503, the available transducing space may be reduced. For example, if another layer is deposited over the middle spring layer 1520 or the sidewall anchor 1503, the top surface of the sidewall anchor is defined as the uncovered surface of the layer deposited over the sidewall anchor 1503. In the exemplary configuration shown in FIG. 15, the actual height of the available transducing space 1560 may be reduced by the thicknesses of the insulation layer 1535, the bottom electrode 1525 and the middle spring layer 1520.

In some embodiments it is possible to have the entire height between the top plate layer 1540 and the top surface of the sidewall anchor 1503 available for the transducing space 1560. For example, the insulation layer may be removed if other features (e.g. motion stopper) are used to prevent from electric shorting between two electrodes); a conductive substrate wafer may itself be used to effectuate a bottom electrode on the substrate (e.g., on the sidewall anchor 1503) without requiring a separate electrode layer; and cantilevers may be made with segments of middle spring layers connected to the sidewall anchor 1503 at sides flush with or lower than the top surface of the sidewall anchor 1503, instead of using a continuous middle spring layer placed on top of the sidewall anchor 1503.

Both substrate 1501 including the sidewall anchor 1503 and the middle spring layer 1520 may be conductive. In this case, the substrate 1501 may serve as a conductor to access the conductive middle spring layer 1520, while the middle spring layer 1520 may serve as the bottom electrode.

The connectors 1530 and 1530a stand on the middle spring layer 1520 and each have a substantially identical connector height. The connectors 1530 and 1530a are each horizontally distanced from the respective sidewall of the sidewall anchor 1503 by a sufficient length. This defines two cantilevers each anchored at the respective side of sidewall anchor 1503 with a back-to-back double cantilever formation. The cantilevers are activated through the respective connector (1530 or 1530a) at an exerting end (e.g., 1522 on the left side cantilever) where the connector (1530 or 1530a) is located. The cantilevers and the respective cavities 1502 and 1502a enable a vertical displacement of the connectors 1530 and 1530a, which transport the top plate 1540 substantially vertically with a piston-like motion, thus changing the transducing space 1560. When the both halves of the ESMUT structure 1500 move in the same phase, the vertical piston-like motion is further assured.

In this particular example shown, top surface of the sidewall anchor 1503 is covered by the middle spring layer 1520, which in turn is covered by the bottom electrode 1525. Furthermore, the top plate 1540 and the connector 1530 do not connect with each other directly but are intervened by the insulation layer 1535 therebetween. The transducing space 1560 is therefore partially occupied by the middle spring layer 1520, the bottom electrode 1525 and the insulation layer 1535. The part of the middle spring layer 1520 covering the top surface of the sidewall anchor 1503, the bottom electrode 1525 and the insulation layer 1535 are optional. In any event, in order to achieve the intended energy transformation, the transducing space 1560 should not be entirely occupied by these extra layers if they are included in the structure.

Figure 16:
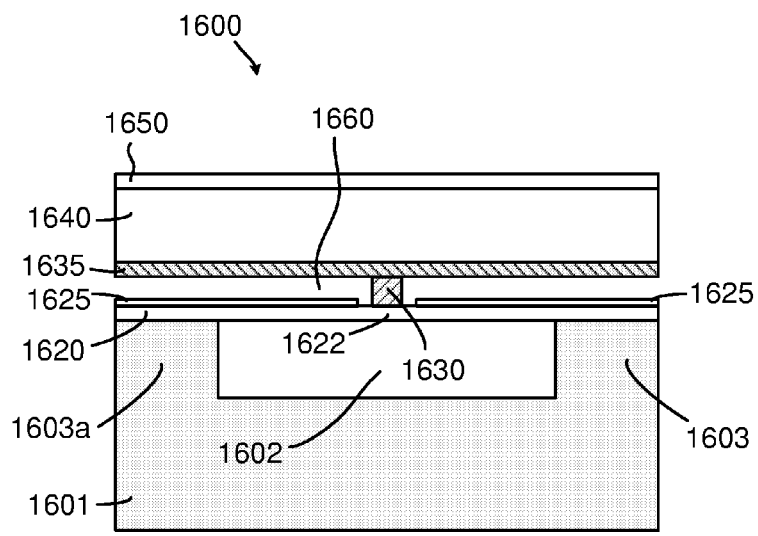
FIG. 16 is an enlarged view of a different selected ESMUT portion of a complete ESMUT element.

FIG. 16 is an enlarged view of a different selected ESMUT portion 1600, which is another part of the complete ESMUT element (not shown). The selected ESMUT portion 1500 shown in FIG. 15 and the selected ESMUT portion 1600 may be taken from the same ESMUT element at shifted locations. The selected ESMUT portion 1600 is built on a substrate 1601, which has a cavity 1602 bordered by two sidewall anchors 1603 and 1603a on two opposite sides. The ESMUT structure portion 1600 further has these components: middle spring layer 1620, bottom electrode 1625 placed on middle spring layer 1620, connector 1630 which stands on top of the middle spring layer 1620, insulation layer 1635 sitting over the connector 1630, top plate 1640 connected to the connector 1630 through an intervening insulation layer 1635, and top electrode 1650.

The connector 1630 stands on the middle spring layer 1620, and is horizontally distanced from the sidewalls of both the sidewall anchor 1603 and the sidewall anchor 1603*a*. The middle spring layer 1620 between the sidewall anchor 1603 and the sidewall anchor 1603*a* defines a double-cantilever anchored at the sidewall anchor 1603 and the sidewall anchor 1603*a*. The double-cantilever is connected head-to-head at location 1622 where the connector 1630 is positioned to form a bridge.

The top plate 1640 is placed over the connector 1630, which separates the top plate 1640 from the middle spring layer 1620 to define a transducing space 1660 below the top plate. The double-cantilever and the cavity 1602 enable a vertical displacement of the connector 1630, which transports the top plate 1640 substantially vertically, thus changing the transducing space and activating a transducing member in the transducer for energy transformation.

The above ESMUT designs can be used as a basic building unit for constructing a variety of micro-electro-mechanical transducers that have a movable mechanical part to transform energy. The ESMUT structure essentially did away with the conventional concept of the cell insulation wall which divides a cMUT element into cells and is required to support and clamp the membrane at the perimeter of each cMUT cell.

As shown below with reference to FIGS. 17-18, the insulation extension in accordance with the present invention may be incorporated in the ESMUT to further improve its performance.

Figure 17:
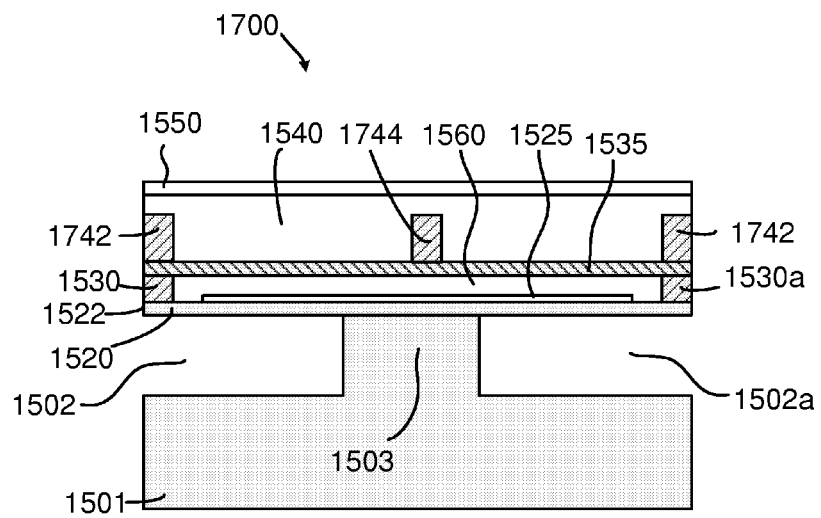
FIG. 17 shows an ESMUT structure using an insulation extension in accordance with the present invention.

FIG. 17 shows an ESMUT structure using an insulation extension in accordance with the present invention. The ESMUT structure 1700 is based on the ESMUT structure 1500 and shares most of the components of the ESMUT structure 1500. The ESMUT structure 1700 has insulation extensions 1742 and 1744 extending into the top plate 1540 to provide additional insulation without increasing the transducing space 1560. As shown, insulation extensions 1742 are aligned with connectors 1530 and 1530*a* and connected thereto through the optional insulation layer 1535. The connectors 1530 and 1530*a* are made of an insulating material and are equivalents of insulating support portions in FIGS. 4-7 and insulation supports or insulation anchors in FIGS. 8-14. The insulation extension 1744 is placed between the insulation extensions 1742 near a middle position where the top plate 1540 including the optional intervening insulation layer 1535 is most likely to contact or come close to contact the bottom electrode 1525.

Figure 18:
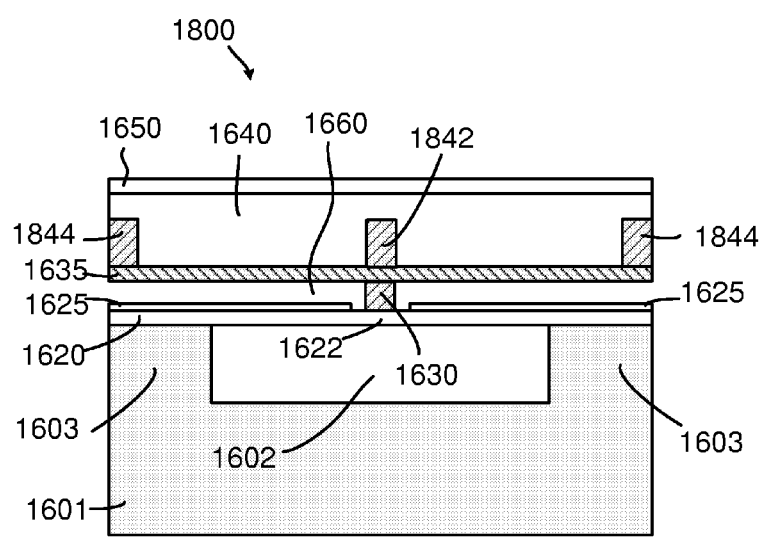
FIG. 18 shows another ESMUT structure using an insulation extension in accordance with the present invention.

FIG. 18 shows another ESMUT structure using an insulation extension in accordance with the present invention. The ESMUT structure 1800 is based on the ESMUT structure 1600 and shares most of the components of the ESMUT structure 1600. The ESMUT structure 1800 has insulation extensions 1742 and 1844 extending into the top plate 1640 to provide additional insulation without increasing the transducing space 1660. As shown, insulation extension 1842 is aligned with connector 1630 and connected thereto through the optional insulation layer 1635. The connector 530 is made of an insulating material and is an equivalent of insulating support portions in FIGS. 4-7 and insulation supports or insulation anchors in FIGS. 8-14. The insulation extensions 1844 are placed at positions where the top plate 1640 including the optional intervening insulation layer 1635 is most likely to contact or come close to contact the bottom electrode 1625.

The insulation extensions 1742, 1744, 1842 and 1844 in the above embodiments allow maximizing breakdown voltage and minimizing parasitic capacitance without reducing transaction performance of the transducer. The insulation extensions 1744 and 1844 are optional if the maximum displacement of the top plate 1540/1640 is limited by other components, such as motion stoppers, to avoid contact between the top plate 1540/1640 (or an intervening layer such as 1535/1635) and the middle spring layer 1520/1620 (or an intervening layer such as 1525/1625). The extra insulation effect of the insulation extensions is particularly helpful when the top plate 1550 or 1650 is a conductive layer (such as a silicon or polysilicon layer) or a nonconductive layer but without sufficient insulation power. It is appreciated that although a certain type of insulation extension is used here for the purpose of illustration, any configuration of insulation extensions in accordance with the present invention may be used in the ESMUT structure. For example, insulation extensions may be alternatively or additionally built in the middle spring layer 1520 or 1620 and/or the substrate anchor 1503 or 1603.

Fabrication Methods:

The micro-electro-mechanical transducer having an insulation extension in accordance with the present invention may be fabricated using a variety of methods. According to one aspect of the present invention, a method for fabricating a micro-electro-mechanical transducer having two electrodes separated by an insulator with an insulation extension comprises the steps of: (1) forming a recess on a major surface of a first conductive layer; (2) forming a standing feature of an insulating material, the standing feature extending from the recess to a free end above the major surface of the first wafer material; and (3) placing a second conductive layer over the free end of the standing feature.

Methods for forming very deep insulation extensions are also described. An exemplary method comprises the steps of: (1) forming a patterned trench over a major surface of a substrate by removing material of the substrate, wherein the patterned trench comprises thin lines of unremoved material of the substrate; (2) oxidizing the thin lines of unremoved material of the substrate in the patterned trench such that the patterned trench constitutes an insulator; (3) patterning and etching the major surface of the substrate such that the insulator has a top end standing above the substrate; and (4) placing a top conductive layer over the top end of the insulator. A suitable substrate for this method is an oxidizable substrate such as a silicon wafer.

Alternatively, the method may also comprise the steps of: (1) forming a trench over a major surface of a substrate by removing material of the substrate; (2) filling the trench with an insulating material; (3) patterning and etching the major surface of the substrate such that the insulating material in the trench has a top end standing above the substrate; and (4) placing a top conductive layer over the top end of the insulator. A suitable substrate for this method is a silicon wafer.

An exemplary method for fabricating an ESMUT in accordance with the present invention comprises the steps of: (1) providing a top plate, a middle spring layer and a substrate; (2) forming a standing feature of an insulating material on a major surface of one of the top plate and the middle spring layer, the standing feature extending from a point below the major surface to a free end beyond the major surface; and (3) joining the top plate, the middle spring layer and the substrate, such that the top plate and the middle spring layer are connected by the standing feature at the free end thereof, and the middle spring layer is connected to the substrate at an opposing side. In the resultant ESMUT, the substrate and the middle spring layer define a cavity therebetween, the cavity is bordered by a sidewall, and the middle spring layer extends from the sidewall to cover the cavity.

Exemplary embodiments of the methods are described below with reference to FIGS. 19-27. The process to form insulation extensions can be incorporated into regular fabrication process of a micro-electro-mechanical transducer such as cMUT process by adding a few steps to form the insulation extensions. As will be shown below, incorporating the steps of forming desirable recesses or cavities with desired patterns on a substrate is an important element of the methods.

It is appreciated that the individual steps illustrated may take place in any order as long as they are physically compatible with each other to accomplish the final structure. Many alternative steps, including but not limited to those specifically illustrated herein, are possible. Furthermore, it is appreciated that many steps described below are optional, including but not limited to those steps that are specifically indicated as optional in the description.

FIGS. 19.1-19.9*a* show a process flow to incorporate insulation extensions of the present invention into a conventional membrane-based cMUT using wafer-bonding technique. The major steps of the process are described as follows.

In step one (FIG. 19.1), desired recess pattern including recesses 1905 and 1906 are formed on the substrate 1901. In the example shown, recesses of two different depths, one (1905) for insulation extensions of insulation supports (anchors) and the other (1906) for insulation extensions at locations where the two electrodes may contact during the transducer operation. The two types of recesses 1905 and 1906 may either be formed in a single step at the same time or formed separately using two steps. There are many suitable methods to make the desired recess pattern on a substrate. In case where an etchable substrate (e.g., a silicon wafer) is used, desired recess pattern can be formed by etching the substrate directly using a proper etching technique.

In step two (FIG. 19.2), an insulation layer 1931 (e.g., thermal oxide, LTO, nitride, TEOS, and SOG) is introduced into the recesses 1905 and 1906 to the desired thickness.

In step three (FIG. 19.3), the insulation layer 1931 is patterned and etched to form insulation supports (anchors) 1932 and motion stoppers 1934, each of which stands in the recesses 1905 and 1906 and extends to a free end.

In step four (FIG. 19.4), another insulation layer 1933 is grown if needed.

In step five (FIG. 19.5), the insulation layer 1933 is patterned if needed leaving a layer 1935 in each recess 1905 and 1906 to form a part of insulation extension.

In step six (FIG. 19.6), an SOI wafer with a desired membrane layer 1919 is bonded over the free ends of the insulation supports (anchors) 1932 and motion stoppers 1934. The SOI wafer is then annealed and etched back to leave the membrane layer 1919 on the insulation supports (anchors) 1932. In this step, vias may be etched to access the bottom electrode if needed (not shown).

Instead of using an SOI wafer, a wafer carrying a functional layer such as a nitride, oxide, metal, parylene or other polymer layer to serve as a desired membrane layer 1919 can be used with a suitable bonding technique to accomplish the above step six.

In step seven (FIG. 19.7), the metal layer 1920 is deposited to form the top electrode. After this step, the membrane layer 1919 between the neighboring cMUT elements may be etched to separate the individual cMUT elements if needed (not shown).

Other variations of the steps may be used. For example, the SOI boding technique used in the above described steps six and seven may be substituted with an alternative surface micromachining process using sacrificial technique. The alternative method, including alternative step six, seven, eight and nine, is described below.

In alternative step six (FIG. 19.6*a*), a sacrificial layer 1939 is deposited over the free ends of the insulation supports (anchors) 1932 and motion stoppers 1934.

In alternative step seven (FIG. 19.7*a*), the membrane layer 1919 is deposited and patterned as desired.

In alternative step eight (FIG. 19.8*a*), vias (not shown) are etched if necessary, and the sacrificial layer 1939 is then removed. Thereafter, the vias are sealed with a proper material.

In alternative step nine (FIG. 19.9*a*), the metal layer 1920 is deposited to form the top electrode. The resultant structure is similar to that in FIG. 19.7.

Much freedom exists in selecting a proper process step and further selecting different materials for each layer used in the step. Especially, different bonding process (e.g., silicon fusion bonding, eutectic bonding, anodic bonding, and thermal compression bonding) may be applied in the process to form the membrane with different materials (e.g., silicon, silicon nitride, oxide, polymer, sapphire, diamond, and SiC).

Similar processes, such as that using wafer bonding and surface micromachining techniques, may be used to fabricate ESMUTs with insulation extensions incorporated therein in accordance with the present invention.

There are many suitable methods to make the desired recess pattern on a substrate. In addition to directly etching the substrate using the proper etching process, the desired recess pattern may also be formed using other methods such as the differential oxidation methods described below with reference to FIGS. 20-22. Because oxide with different oxidation thickness consumes different amounts of the oxidized material, a pattern (e.g., recesses) may be formed on an oxidizable conductive surface using differential oxidation. This is accomplished by using a nitride layer and/or an oxide layer as masks for additional oxidation. A nitride layer can essentially block oxidation underneath, and an oxide layer can slow down the oxidation underneath. Using oxide or nitride layers as oxidation masks, oxidation with different thickness can be formed at desired locations on the conductive (e.g. silicon) material surface.

Since the oxidation process consumes the oxidized material, it can be viewed as an equivalent to directly etching of the material. However, oxidation process is generally easier to control and has better accuracy than direct etching. Therefore, using oxidation method to form recesses may be preferred over direct etching processes for fabricating transducers (such as cMUTs) that require high accuracy and uniformity of patterns, recesses and material distributions on an electrode surface and substrate.

FIGS. 20.1-20.3 show an exemplary process for forming a recess on a substrate. The method is particularly suitable for forming a recess on an oxidizable substrate such as silicon substrate. The process can also be used to form a recess on an oxidizable top plate layer or middle spring layer.

In step one (FIG. 20.1), a first oxide layer 2010 is grown over a major surface of the substrate 2001. The oxide layer 2010 is patterned and has an opening 2015 where the substrate is uncovered by oxide.

In step two (FIG. 20.2), a second oxide layer 2020 is grown over the first oxide layer 2010 (including the opening 2015). The second oxide layer 2020 has a first depth 2030 reaching into the substrate 2001 at where the opening 2015 is located, and a second depth reaching into the substrate 2001 at positions covered by the first oxide layer 2020. Because the first oxide layer 2020 slows down the oxidation process, the first depth 2030 will be greater than the second depth. The difference between the two depths will be the basis for forming a recess in the next step.

In step three (FIG. 20.3), the first oxide layer 2010 and the second oxide layer 2020 are removed to form a recess 2040.

FIGS. 21.1-21.3 show another exemplary process for forming a recess on a substrate. The method is particularly suitable for forming a recess on an oxidizable substrate such as silicon substrate. The process can also be used to form a recess on an oxidizable top plate layer or middle spring layer.

In step one (FIG. 21.1), a first oxide layer 2110 and a nitride layer 2120 are grown over a major surface of the substrate 2101. The oxide layer 2110 is patterned and has an opening 2115 where the substrate is uncovered by oxide. The nitride layer 2120 has an opening coincide with the opening 2115 of the first oxide layer 2110.

In step two (FIG. 21.2), a second oxide layer 2130 is grown over the first oxide layer 2110 and the nitride layer (including the opening 2115). The second oxide layer reaches a desired depth into the substrate 2001 at where the opening 2015 is located. The nitride layer 2120 essentially stops further oxidation in other areas. The depth of the second oxide layer will be the basis for forming a recess in the next step.

In step three (FIG. 21.3), the nitride layer 2120, the first oxide layer 2110 and the second oxide layer 2130 are removed to form a recess 2140.

The above methods may be repeated or combined to form more complex recess patterns with various depths. FIGS. 22.1-22.5 show a process to fabricate a desired recess pattern on a silicon substrate using oxidation process. This method can also be applied to other substrates that can be oxidized. The major steps of the process are described below.

In step one (FIG. 22.1), a thermal oxide layer 2231 is formed, and patterned if desired, on the substrate 2201 to a desired thickness.

In step two (FIG. 22.2), another thermal oxide layer 2232 is grown over the patterns of the first thermal oxide layer 2231 to a desired thickness.

In step three (FIG. 22.3), the resultant thermal oxide layer is 2231 and 2232 are further patterned to a desired pattern for forming the desired recess is in the next steps.

In step four (FIG. 22.4), another thermal oxide layer 2233 is formed over the oxide pattern to a desired thickness. This is to further define the different depths of the desired recesses to be formed.

In step five (FIG. 22.5), the remaining oxide is removed to form the desired recess pattern on silicon substrate 2201. The recess pattern includes recesses of two different depths, one (2205) for forming insulation extensions of insulation supports (anchors) and the other (2206) for insulation extensions at locations where the two electrodes may contact during the transducer operation.

FIGS. 23.1-23.5 show another process to fabricate a desired recess pattern on a silicon substrate using O2 implantation and oxidation process. This method can also be applied to other substrates that can be oxidized. The major steps of the process are described below.

In step one (FIG. 23.1), patterned (selective) O2 implantation is performed over the silicon substrate 2301 using a patterned mask 2309.

In step two (FIG. 23.2), thermal oxidation is performed over the silicon substrate 2301 which has been treated with O2 implantation. The thermal oxidation forms an oxide layer 2331 that has thicker oxide formation in the selective areas where O2 implantation has taken place.

In step three (FIG. 23.3), the oxide layer 2331 is patterned.

In step four (FIG. 23.4), further thermal oxidation is performed over the patent oxide layer 2331.

In step five (FIG. 23.5), the existing oxide is removed to form the desired recess pattern on silicon substrate 2301. The recess pattern includes recesses of two different depths, one (2305) for forming insulation extensions of insulation supports (anchors) and the other (2306) for insulation extensions at locations where the two electrodes may contact during the transducer operation.

FIGS. 24.1-24.3 show another process to fabricate a desired recess pattern on a silicon substrate using O2 implantation and Local Oxidation of Silicon (LOCOS). This method can also be applied to other substrates that can be oxidized. The major steps of the process are described below.

In step one (FIG. 24.1), patterned (selective) O2 implantation is performed over the silicon substrate 2401 using a patterned mask 2409.

In step two (FIG. 24.2), a patterned nitride protection layer 2431 is deposited over the silicon substrate 2401 which has been treated with O2 implantation. A LOCOS process is then performed over the silicon substrate 2401 the patterned nitride protection layer 2431. The LOCOS process forms an oxide pattern that has two types of localized oxidation areas, including a thicker oxide formation 2032 in the selective areas where O2 implantation has taken place and a thinner oxide formation 2034 in the other unprotected areas where no O2 implementation has taken place. The above process can be replaced with two separate LOCOS processes with desired oxide thickness to form the two types of localized oxidation separately.

In step three (FIG. 24.3), the nitride and the oxide are removed to form the desired recess pattern on silicon substrate 2401. The recess pattern includes recesses of two different depths, one (2405) for forming insulation extensions of insulation supports (anchors) and the other (2406) for insulation extensions at locations where the two electrodes may contact during the transducer operation.

Methods to Form Very Thick High Insulation Extensions:

In the methods described above, insulation extensions are fabricated by growing or depositing an insulating material. The thickness of the insulation extensions is thus limited by the film deposition or film growth process. In some applications, however, a very thick insulation may be needed to prevent the electrical breakdown. Therefore, a different process is needed to fabricate very thick insulation extensions in micro-electro-mechanical transducers.

FIGS. 25.1-25.7 show an exemplary method to form very deep insulation extensions in a conventional cMUT with a flexible membrane surface. The exemplary method forms deep insulation extensions by etching a desired pattern on the substrate, and then to totally oxidizing the pattern. The patterned area on the substrate may be filled by a thermal oxide with a well-designed pattern. The major steps of the exemplary method are described as follows.

In step one (FIG. 25.1), a desired recess pattern 2531 is first formed on substrate 2501. The recess pattern 2531 may be formed by a variety of techniques, including direct etch process, oxidation or LOCOS. This step is optional.

In step two (FIG. 25.2), a desired silicon pattern is etched over the surface of the substrate 2501 and the recess pattern 2531. The silicon pattern has multiple deep patterned trenches etched to a desired thickness at selected locations including over the recesses of the recess pattern 2531. Each patterned trench has voids where the original material of the substrate 2501 has been removed but also has narrow lines 2537 of unremoved original material of the substrate 2501.

In step three (FIG. 25.3), the patterned trenches having narrow lines 2532 of unremoved substrate material is completely oxidized using thermal oxidation to form an oxide layer 2533 which has variable depths. In particular, the oxide layer 2533 has deep oxide portions 2532 and 2534 filling the spaces that used to be deep patterned trenches. In this step, a filler material may be added if the thermal oxide did not totally fill the trenches. The surface of the oxide layer 2533 may be polished if needed. If step one of FIG. 25.1 is not done previously to create the desired variation of surface heights, the oxide at locations corresponding to recesses 2531 in FIG. 25 may be etched to the desired height in this step.

In step four (FIG. 25.4), the oxide layer 2533 is patterned and selected portions the substrate 2501 under the oxide layer 2533 is etched to a desired thickness. After this step, the deep oxide portions 2532 and 2534 remain in the substrate 2501. Besides direct etch process, oxidation or LOCOS process may be used to etch the substrate in the step.

In step five (FIG. 25.5), the remaining oxide is again patterned and the underlying substrate is etched to a desired thickness to form a clearer formation of the deep oxide portions 2532 and 2534 which are to become insulation supports (anchors) and insulation extensions. If needed, a thin oxidation layer may be grown and patterned after this step.

In step six (FIG. 25.6), an SOI wafer is bonded over the free ends of deep oxide portions 2532 and 2534. The handle wafer and box layer (not shown) of the SOI wafer are removed to leave the membrane layer 2519. As shown, deep oxide portions 2532 each provides an insulation support (anchor) above the substrate 2501 and a deep insulation extension extending into the substrate 2501, and deep oxide portions 2534 each provides a deep insulation extension extending into the substrate 2501 at locations in the middle of neighboring insulation supports (anchors). If desired, deep oxide portions 2534 may also have a section above the substrate 2501 to form motion stoppers.

In step seven (FIG. 25.7), the metal layer 2520 is deposited and patterned if desired to form the top electrode. The membrane layer is then etched to separate individual cMUT elements if needed.

It is appreciated that the above illustrated process is only exemplary. Many variations are possible even within each step of the process. For example, different patterns may be used in the first four steps (step one through step four) to achieve a formation that can be used in step five to form the clear formation of the deep oxide portions 2532 and 2534. One example of such alternative patterning is illustrated below with reference to FIGS. 25.1a-25.4a, which are alternatives to FIGS. 25.1-25.4. In addition, a surface micromachining process as illustrated in the steps in FIGS. 19.6a-19.8a may be used to replace the step in FIG. 25.6 to form the cMUT with very high insulation extension.

In contrast to the methods using film deposition or film growth to control the thickness of the insulation extension, the above method defines the thickness of the insulation extensions by the etching process. The insulation extensions may be fabricated to a much greater range of thickness, practically as thick as whatever thickness the cMUTs design optimization may require.

The above method can be easily adapted to cMUT designs. For example, similar insulation extensions may be formed on either the rigid top plate or the middle spring layer of ESMUT (cMUT with embedded springs as shown FIGS. 15-18) using the same method. To be compatible with the method, the host layer (the layer of the ESMUT in which the insulation extensions are formed) may be made of any material (e.g., silicon, Ge, GaAs or any other semiconductor material) that can be oxidized.

FIGS. 26.1-26.7 show another method to form deep insulation extensions by etching. The major steps of the method are described as follows.

In step one (FIG. 26.1), trenches 2631 are etched on the substrate 2601

In step two (FIG. 26.2), trenches 2631 are filled with a desired dielectric material 2633 (e.g., glass frit, LTO, SOG, silicon nitride, PSG or combination of multiple layers of those materials).

In step three (FIG. 26.3), the surface of the dielectric material 2632 is polished if needed.

In step four (FIG. 26.4), patterning and etching is performed on the filler material 2633 to leave deep insulators 2632 and 2634 (including corresponding insulation extensions) in the substrate 2601. Two different types of deep insulators 2632 and 2634 of different heights are formed in the step.

In step five (FIG. 26.5), the substrate 2601 is etched to a desired thickness to further define the insulators 2632 and 2634. Each insulator 2632 or 2634 now has two portions well defined. A first portion is an insulation extension extending into the substrate 2601 and the second abortion an insulation support or anchor extending above the substrate 2601.

In step six (FIG. 26.6), additional etching is performed on the substrate 2601 to form peripheral trenches 2635 surrounding the insulation extensions.

In step seven (FIG. 26.7), an SOI wafer is first bonded over the free ends of insulators 2632, and the handle wafer and box oxide layer (not shown) are then removed to from the membrane 2619. A metal layer 2620 is then deposited and patterned if needed to form the top electrode. The membrane layer 2019 maybe etched to separate the cMUT elements if needed.

Like the method in FIGS. 25.1-25.7, the above method defines the insulation extension thickness by the etch depth instead of the thickness of a deposition material. This method can thus make very thick insulation extensions, which may be essential to make high temperature cMUTs or cMUTs with very large breakdown voltage.

A wide range of filler materials, such as fret glass, SOG, LTO, nitride, TEOS, etc., are available to be used in the method to fill the trenches. The trenches may also be filled with a combination of multiple layers of the materials, at least one of which should be an insulating material.

The methods shown in FIG. 25-26 both utilize using wafer-bonding technologies to make the cMUT with insulation extensions. Once the insulation extensions are fabricated, however, the cMUT may be completed using surface micromachining based on sacrificial technique.

The fabrication methods shown in FIGS. 19-26 are examples of incorporating the insulation extensions of the present invention in a conventional cMUT (a cMUT with a flexible membrane). The methods, however, can be easily adapted to other cMUT designs. In particular, similar insulation extensions may be formed on either the top plate or middle spring layer of an ESMUT (a CMUT with embedded springs as disclosed in the several PCT patent applications referenced herein) using the same methods. The host layer in which the insulation extensions are formed may be made of any suitable material, but the insulation extensions are particularly benefiting if the host layer is made of the conductive material such as silicon, Ge, GaAs or other semiconductor material.

FIGS. 27.1-27.16 show a wafer-bonding process for fabricating an ESMUT having insulation extensions in accordance with the present invention. The ESMUT also has a self-alignment feature incorporated in the fabrication process, but the self alignment feature is included for illustration only and is not required by insulation extensions. The process may also incorporate other features such as trench sealing. The steps of the process are described below.

In step one (FIG. 27.1), process starts with an SOI wafer 2780 carrying a silicon layer 2740 which is to become the top plate layer 2740 of the resultant cMUT structure. An oxide layer 2781 and a nitride layer 2782 are grown on the bottom of the top plate 2740. Alternatively, this step may start with a prime wafer, which can be ground and polished to a desired thickness for the top plate layer in a later step.

In step two (FIG. 27.2), the oxide layer 2781 and nitride layer 2782 are patterned according to the cMUT design to expose certain areas of the top plate layer 2740.

In step three (FIG. 27.3), the exposed areas of the top plate layer 2740 is oxidized to a desired thickness.

In step four (FIG. 27.4), the nitride and oxide layers are removed to form recesses 2741 on the bottom surface of the top plate layer 2740. The recesses 2741 will be the bases to receive insulators including insulation extensions and insulation supports (contractors).

In step five (FIG. 27.5), standing features 2731 of an insulation material are formed over the recesses 2741 of the top plate layer 2740. These standing features 2731 will provide both the plate-spring connectors 2730 (which are insulators) and the insulation extensions within the recesses. One way to form such standing features 2731 is to grow an oxide layer.

In step six (FIG. 27.6), another oxide layer 2732 is grown over the recesses 2741 of the top plate layer 2740. This optional oxide layer 2732 may be patterned to become an additional part of the insulation extension within the recesses 2741. The optional oxide layer 2732 may improve the insulation by preventing electrical leaking on the surface.

In step seven (FIG. 27.7), another SOI wafer 2785 carrying a silicon layer 2721 is bonded to the plate-spring connectors 2730. The silicon layer 2721 is to become the middle spring layer 2720 in the final ESMUT structure to form the embedded springs (cantilevers). To serve this purpose, the silicon layer 2721 should have a proper thickness.

In step eight (FIG. 27.8), SOI wafer 2785 is etched back to remove the carrier layer and the oxide layer to leave the silicon layer 2721 which is to become the middle spring layer 2720. If needed, silicon doping can be done in selected areas of the silicon layer 2721 in this step.

In step nine (FIG. 27.9), an oxide layer 2786 and a nitride layer 2787 are formed and patterned over the silicon layer 2721, leaving selected areas 2788 of the silicon layer 2721 accessible.

In step ten (FIG. 27.10), the accessible areas 2788 of the silicon layer 2721 are oxidized to a desired thickness.

In step eleven (FIG. 27.11), the oxide and nitride layers are removed at selected locations leaving remaining oxide and nitride on top of areas 2713 of the silicon layer 2721. The areas 2713 will become sidewall anchors 2703 in the final ESMUT structure. The other uncovered areas of silicon layer 2721 are now exposed for the next step.

In step twelve (FIG. 27.12), the exposed areas of the silicon layer 2721 is oxidized to a desired thickness.

In step thirteen (FIG. 27.13), both the oxide and nitride layers over areas 2713 and the new oxidized layer formed in step twelve are removed to form the middle spring layer 2720 having thicker part features that will become the sidewall anchors in 2703 and cantilever dividers 2722. The cantilever dividers 2725 may have two functions at the same time: (1) serving as motion stoppers; and (2) defining the length of the spring with 2703.

In step fourteen (FIG. 27.14), a prime wafer 2701 with a desired thickness is bonded. This layer becomes the substrate 2701 for the final ESMUT structure. After this step, the process to finish the fabrication is similar to the final steps of some of the other exemplary fabrication methods described in this description. One example is briefly described below.

In step fifteen (FIG. 27.15), the top SOI wafer 2780 is etched back to remove the carrier layer and the oxide layer to form the top plate 2740.

In step sixteen (FIG. 27.16), metal layer 2750 is deposited and patterned if needed to form interconnections. Trenches 2715 are formed between ESMUT elements to separate the individual ESMUT elements.

Several other options are available for the above step fourteen. Example, instead of bonding a prime wafer, a processed wafer with through-wafer interconnections formed therein may be for fusion bonded to the middle spring layer 2720. The processed wafer and the middle spring layer 2720 define a cavity pattern which corresponds to the shapes of cantilever-forming areas. This step may also be done with other wafer-bonding technologies (e.g. eutectic bonding, thermal compression bonding, and anodic bonding).

Alternatively, a wafer with desired metal patterns or integrated circuits (ICs) or a PCB board with desired circuits may be bonded to the middle spring layer 2720. The wafer may be made of materials such as glass, sapphire, or silicon. Alternatively, a silicon wafer having integrated circuits (ICs) built therein is bonded to the middle spring layer 2720.

Instead forming the insulation extensions on the top plate 2740, the similar process may be performed to make insulation extensions on the middle spring layer 2720.

The material selection and process method selection in each step for the fabrication methods shown above in FIGS. 27.1-27.16 are similar to those described herein in association with fabrication methods with other micro-electro-mechanical structures. Again, although a cMUT is used for the purpose of illustration in the above described processes, the methods are not limited to such. The micro-electro-mechanical structures can also by fabricated by using only a part of each process, or different step sequences of the processes shown in FIGS. 27.1-27.16. In addition, in stead of using a SOI wafer, the middle spring layer of the micro-electro-mechanical structures having embedded springs can be made of a silicon wafer with highly doped layer or silicon wafer. Cantilever areas on the middle spring layer can be subsequently formed using selective silicon etching.

The micro-electro-mechanical transducer in accordance with the present invention has been described in detail along with the figures and exemplary embodiments. The transducer potentially can alleviate or eliminate a number of problems with existing technology. The invention has eliminated the necessity of forming an addressable transducer element using a great number of smaller cells. Using the technology, either a much fewer cells are just a single cell may be necessary for each addressable transducer element. The design of the micro-electro-mechanical transducer of the present invention is particularly suitable for application in capacitive micromachined ultrasonic transducers (cMUT), but can also be used for other micro-electro-mechanical devices which have a movable mechanical part to transform energy.

In particular, the micro-electro-mechanical transducer in accordance with the present invention may be fabricated using the fabrication methods or incorporated in the micro-electro-mechanical transducer as disclosed in international patent applications (PCT) No. PCT/IB2006/051566, entitled THROUGH-WAFER INTERCONNECTION, filed on May 18, 2006; No. PCT/IB2006/051567, entitled METHODS FOR FABRICATING MICRO-ELECTRO-MECHANICAL DEVICES, filed on May 18, 2006; No. PCT/IB2006/051568, entitled MICRO-ELECTRO-MECHANICAL TRANSDUCERS, filed on May 18, 2006; and No. PCT/IB2006/051569, entitled MICRO-ELECTRO-MECHANICAL TRANSDUCERS, filed on May 18, 2006. These patent applications are hereby incorporated herein by reference.

In the foregoing specification, the present disclosure is described with reference to specific embodiments thereof, but those skilled in the art will recognize that the present disclosure is not limited thereto. Various features and aspects of the above-described disclosure may be used individually or jointly. Further, the present disclosure can be utilized in any number of environments and applications beyond those described herein without departing from the broader spirit and scope of the specification. We claim all such modifications and variations that fall within the scope and spirit of the claims below. The specification and drawings are, accordingly, to be regarded as illustrative rather than restrictive. It will be recognized that the terms 'comprising,' 'including,' and 'having,' as used herein, are specifically intended to be read as open-ended terms of art.

The invention claimed is:

1. An electrostatic transducer comprising:
a first conductive layer having a first major surface;
a second conductive layer having a second major surface opposing the first major surface of the first conductive layer, the first major surface and the second major surface defining an electrode separation gap therebetween; and
an insulating support including:
a main portion disposed within the electrode separation gap between the first conductive layer and the second conductive layer; and
an insulation extension portion extending into a cavity formed in the first conductive layer, wherein:
the cavity is directly under the main portion of the insulating support;
the first conductive layer includes a first conductive surface that is directly under the main portion, and the second conductive layer includes a second conductive surface that is directly over the main portion; and
the first conductive surface that is directly under the main portion of the insulating support, and that is nearest to the second conductive surface that is directly over the main portion of the insulating support, is separated from the second conductive surface that is directly over the main portion of the insulating support by a distance greater than the electrode separation gap.

2. The electrostatic transducer of claim 1 wherein the first conductive layer includes a semiconductor layer and a supplemental conductive layer having a conductivity significantly higher than that of the semiconductor layer.

3. The electrostatic transducer of claim 1 wherein:
the first conductive layer includes a semiconductor layer; and
the semiconductor layer of the first conductive layer is thicker than the insulation extension portion such that the insulation extension portion is contained therein.

4. The electrostatic transducer of claim 3 wherein the semiconductor layer of the first conductive layer includes a silicon/polysilicon layer.

5. The electrostatic transducer of claim 4 wherein the insulation extension portion extends into the silicon/polysilicon layer.

6. The electrostatic transducer of claim 1 wherein the distance greater than the electrode separation gap is at least 25% greater than the electrode separation gap.

7. The electrostatic transducer of claim 1 wherein the main portion of the insulating support comprises a first insulating material, and the insulation extension portion comprises a second insulating material which is different from the first insulating material.

8. The electrostatic transducer of claim 1 wherein the main portion of the insulating support is connected to the insulation extension portion.

9. The electrostatic transducer of claim 1 wherein the cavity and the insulation extension portion have a cross-sectional size greater than that of the main portion of the insulating support.

10. The electrostatic transducer of claim 1 wherein the insulation extension portion comprises a solid material completely filling the cavity.

11. The electrostatic transducer of claim 1 wherein the insulation extension portion comprises a solid material partially filling the cavity leaving a partial void therein.

12. The electrostatic transducer of claim 1 wherein the insulation extension portion is a first insulation extension portion extending into the first conductive layer and the insulating support includes a second insulation extension portion extending into a cavity in the second conductive layer.

13. The electrostatic transducer of claim 12 wherein the first insulation extension portion comprises a first insulating material and the second insulation extension portion comprises a second insulating material which is different from the first insulating material.

14. The electrostatic transducer of claim 1 wherein an additional cavity is formed in the first conductive layer with an additional insulation extension portion extending into the additional cavity, the additional cavity and the additional insulation extension portion are located at a position where the first conductive layer and the second conductive layer are most likely to contact or come close to contacting each other during operation of the electrostatic transducer—since the insulation extension portion (842, 942, FIGS. 8-10) are not located directly under the main portion (830, 930) like the insulation extension portion (840, 940) of claim 1.

15. The electrostatic transducer of claim 1 further comprising a motion stopper extending partially across the electrode separation gap.

16. The electrostatic transducer of claim 1 which is a capacitive micromachined ultrasonic transducer, wherein the first conductive layer serves as a bottom electrode and the second conductive layer serves as a movable top electrode.

17. The electrostatic transducer of claim 16 wherein the second conductive layer comprises a resilient membrane supported by the insulating support.

18. The electrostatic transducer of claim 1 wherein the cavity is formed in the semiconductor layer by oxidation.

19. The electrostatic transducer of claim 1 wherein the insulating support and the insulation extension are oxide grown at the cavity.

20. A capacitive micromachined ultrasonic transducer comprising:
a lower layer including a substrate and serving as a bottom electrode;
a top layer including a membrane and serving as a top electrode, the membrane being adapted for vibrating in relation to the substrate upon a transducing excitation, the lower layer having a first major surface, and the top layer having a second major surface defining an electrode separation gap therebetween; and an insulator having a main portion and an insulation extension portion, the main portion being disposed within the electrode separation gap between and supporting the lower layer and the top layer, and the insulation extension portion extending beyond the electrode separation gap and into at least one cavity formed in at least one of the substrate or the membrane, respectively, the at least one cavity formed respectively directly under or directly above the main portion of the insulating support, wherein:

the at least one cavity includes a first conductive surface respectively directly under or directly above the main portion of the insulator; and an opposing one of the first major surface or the second major surface includes a second conductive surface respectively directly under or directly above the main portion and separated from a nearest portion of the first conductive surface by a distance greater than the electrode separation gap.

21. The capacitive micromachined ultrasonic transducer of claim 20 wherein:

the at least one cavity comprises a first cavity in the substrate and a second cavity in the membrane; and the insulation extension portion comprises a first insulation extension portion extending into the first cavity in the substrate and a second insulation extension portion extending into the second cavity in the membrane.

22. The capacitive micromachined ultrasonic transducer of claim 20 wherein the substrate of the lower layer comprises a silicon/polysilicon layer.

23. The capacitive micromachined ultrasonic transducer of claim 20 wherein the cavity is formed in the at least one of the substrate or the membrane by oxidation.

24. The capacitive micromachined ultrasonic transducer of claim 20 wherein the main portion and the insulation extension of the insulator are oxide grown at the cavity.

25. The capacitive micromachined ultrasonic transducer of claim 20, wherein the distance greater than the electrode separation gap is at least 25% greater than the electrode separation gap.

26. A method for fabricating a micro-electro-mechanical transducer, the method comprising:

forming a recess below a major surface of a first conductive layer;

forming a standing feature of an insulating material over the recess, the standing feature having an insulation extension portion extending from within the recess to the major surface, and a main portion extending from the major surface to a free end above the major surface; and placing a second conductive layer over the free end of the standing feature, wherein:

the major surface of the first conductive layer and an opposing surface of the second conductive layer define an electrode separation gap therebetween, the main portion is a portion of the standing feature directly above the recess and within the electrode separation gap, and a first conductive surface directly under the main portion of the standing feature is separated, at a nearest point, from a second conductive surface, directly over the free end of the standing feature, by a distance greater than the electrode separation gap.

27. The method of claim 26 wherein the first conductive layer comprises a silicon/polysilicon layer.

28. The method of claim 26 wherein the forming the standing feature comprises:

growing an insulation layer over the recess; and patterning and etching the insulation layer.

29. The method of claim 26 wherein the placing the second conductive layer over the free end of the standing feature comprises:

bonding a composite wafer having a functional layer to the free end of the standing feature; and etching back the composite wafer to leave the functional layer on the standing feature.

30. The method of claim 29 wherein the placing the second conductive layer further comprises depositing a metal layer over the functional layer.

31. The method of claim 29 wherein the functional layer on the standing feature comprises a silicon/polysilicon layer.

32. The method of claim 29 wherein the functional layer on the standing feature is a membrane layer adapted for vibrating in relation to the first conductive layer upon a suitable transducing excitation.

33. The method of claim 26 wherein the placing the second conductive layer over the free end of the standing feature comprises:

depositing a sacrificial layer over the first conductive layer and the standing feature;

depositing a functional layer over the sacrificial layer; and removing the sacrificial layer to leave the functional layer over the free end of the standing feature.

34. The method of claim 33 wherein the placing the second conductive layer further comprises depositing a metal layer over the functional layer.

35. The method of claim 33 wherein the functional layer comprises a silicon, polysilicon, or nitride layer.

36. The method of claim 33 wherein the functional layer on the standing feature is a membrane layer adapted for vibrating in relation to the first conductive layer upon a suitable transducing excitation.

37. The method of claim 26 wherein the forming the recess on the major surface of the first conductive layer comprises:

growing and patterning a first oxide layer over the major surface of the first conductive layer, the first oxide layer having an opening leaving a corresponding part of the major surface of the first conductive layer uncovered;

growing a second oxide layer over the first oxide layer including the opening such that the second oxide layer has a first depth into the first conductive layer at where the opening is located and a second depth into the first conductive layer at positions covered by the first oxide layer, the first depth being greater than the second depth; and removing the first oxide layer and the second oxide layer.

38. The method of claim 26 wherein the forming the recess on the major surface of the first conductive layer comprises:

growing a first oxide layer over the major surface of the first conductive layer;

growing a nitride layer over the first oxide layer;

patterning the first oxide layer to form an opening leaving a corresponding part of the major surface of the first conductive layer uncovered;

patterning the nitride layer to form an opening coincide with the opening of the first oxide layer;

growing a second oxide layer over the opening of the first oxide layer and the nitride layer such that the second oxide layer reaches a desired depth into the first conductive layer at where the opening is located; and removing the nitride layer, the first oxide layer and the second oxide layer.

39. The method of claim 26 in which the forming the recess below the major surface of the first conductive layer further comprises forming the recess by oxidation.

40. The method of claim 26 in which the forming the standing feature of the insulating material further comprises using oxide growth to form the standing feature.

41. The method of claim 26, wherein the distance greater than the electrode separation gap is at least 25% greater than the electrode separation gap.

42. A method for fabricating a micro-electro-mechanical transducer having two electrodes separated by an insulator with an insulation extension, the method comprising:

forming a patterned trench over a major surface of a substrate by removing material of the substrate, wherein the patterned trench comprises thin lines of unremoved material of the substrate;

oxidizing the thin lines of unremoved material of the substrate in the patterned trench such that the patterned trench constitutes an insulator;

patterning and etching the major surface of the substrate such that the insulator has a top end standing above the substrate; and placing a top conductive layer over the top end of the insulator.

43. A method for fabricating a micro-electro-mechanical transducer, the method comprising:

forming a trench over a major surface of a substrate by removing material of the substrate;

filling the trench with an insulating material;

patterning and etching the major surface of the substrate such that the insulating material in the trench has a standing feature with a top end standing above the substrate; and placing a top conductive layer over the top end of the standing feature of the insulating material, wherein:

the major surface of the substrate and an opposing surface of the top conductive layer define an electrode separation gap therebetween, and the standing feature of the insulating material includes an insulation extension portion that extends into the trench beyond the electrode separation gap, and a main portion, directly above the trench, and that extends from the major surface to the opposing surface, wherein:

a first conductive surface of the trench directly under the main portion is separated from a second conductive surface of the opposing surface directly above the main portion, and a separation between a nearest portion of the first conductive surface and the second conductive surface is by a distance greater than the electrode separation gap.

44. The method of claim 43 in which the filling the trench with the insulating material further comprises using oxide growth to form the standing feature.

45. The method of claim 43, wherein the distance greater than the electrode separation gap is at least 25% greater than the electrode separation gap.

* * * * *